United States Patent
Rothstein

(10) Patent No.: US 10,779,942 B2
(45) Date of Patent: Sep. 22, 2020

(54) DEVICES AND METHODS FOR TRANSCATHETER VALVE LOADING AND IMPLANTATION

(71) Applicant: Medtronic Vascular, Inc., Santa Rosa, CA (US)

(72) Inventor: Paul Rothstein, Elk River, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 121 days.

(21) Appl. No.: 15/376,736

(22) Filed: Dec. 13, 2016

(65) Prior Publication Data

US 2017/0165066 A1    Jun. 15, 2017

Related U.S. Application Data

(60) Provisional application No. 62/267,200, filed on Dec. 14, 2015.

(51) Int. Cl.
*A61F 2/24*    (2006.01)
*A61F 2/95*    (2013.01)

(52) U.S. Cl.
CPC .......... *A61F 2/2439* (2013.01); *A61F 2/2415* (2013.01); *A61F 2/2418* (2013.01); *A61F 2002/9511* (2013.01)

(58) Field of Classification Search
CPC .... A61F 2/2427; A61F 2/2439; A61F 2/2418; A61F 2/95; A61F 2002/9511
See application file for complete search history.

(56) References Cited

U.S. PATENT DOCUMENTS

| | | | |
|---|---|---|---|
| 5,035,706 | A | 7/1991 | Giantureo et al. |
| 5,693,084 | A | 12/1997 | Chuter |
| 5,776,186 | A | 7/1998 | Uflacker |
| 6,280,465 | B1 | 8/2001 | Cryer |
| 6,517,550 | B1 | 2/2003 | Konya et al. |
| 6,733,521 | B2 | 5/2004 | Chobotov et al. |
| 6,740,111 | B1 | 5/2004 | Lauterjung |
| 7,033,390 | B2 | 4/2006 | Johnson et al. |
| 7,329,275 | B2 | 2/2008 | Yee |

(Continued)

FOREIGN PATENT DOCUMENTS

| | | |
|---|---|---|
| CN | 1961847 A | 5/2007 |
| CN | 101045022 | 10/2007 |

(Continued)

OTHER PUBLICATIONS

PCT/US2016/066323, The International Search Report and the Written Opinion of the International Searching Authority, dated Nov. 8, 2017.

(Continued)

*Primary Examiner* — Sarah A Simpson
(74) *Attorney, Agent, or Firm* — Dicke, Billig & Czaja, PLLC

(57) ABSTRACT

The present disclosure relates to numerous delivery devices and methods for transcatheter prosthetic heart valve loading, deployment and delivery utilizing at least one suture. Disclosed delivery devices utilize improved suture routing methods and configurations that reduce suture tangling and also provide the ability to adjust the prosthetic heart valve expansion and contraction prior to the final release of the prosthetic heart valve from the delivery device.

9 Claims, 29 Drawing Sheets

(56) References Cited

U.S. PATENT DOCUMENTS

| | | | |
|---|---|---|---|
| 7,503,929 B2 | 3/2009 | Johnson et al. | |
| 7,722,666 B2 * | 5/2010 | Lafontaine | A61F 2/2418 623/2.11 |
| 8,403,981 B2 | 3/2013 | Forster et al. | |
| 2005/0119722 A1 | 6/2005 | Styrc et al. | |
| 2005/0137687 A1 | 6/2005 | Salahieh et al. | |
| 2005/0137690 A1 * | 6/2005 | Salahieh | A61F 2/2418 623/2.11 |
| 2007/0100427 A1 | 5/2007 | Perouse | |
| 2007/0233223 A1 | 10/2007 | Styrc | |
| 2008/0147183 A1 | 6/2008 | Styrc | |
| 2009/0048656 A1 | 2/2009 | Wen | |
| 2009/0319037 A1 * | 12/2009 | Rowe | A61F 2/2445 623/2.11 |
| 2010/0249915 A1 | 9/2010 | Zhang | |
| 2010/0286768 A1 | 11/2010 | Alkhatib | |
| 2011/0040366 A1 * | 2/2011 | Goetz | A61F 2/2418 623/1.12 |
| 2011/0106246 A1 | 5/2011 | Malewicz et al. | |
| 2012/0277734 A1 | 11/2012 | Goetz et al. | |
| 2013/0245752 A1 | 9/2013 | Goetz et al. | |
| 2013/0338755 A1 * | 12/2013 | Goetz | A61F 2/2439 623/1.11 |
| 2014/0249622 A1 | 9/2014 | Carmi et al. | |
| 2014/0330368 A1 | 11/2014 | Gloss et al. | |
| 2015/0112430 A1 | 4/2015 | Creaven et al. | |
| 2015/0238315 A1 | 8/2015 | Rabito et al. | |
| 2015/0265442 A1 | 9/2015 | Styrc | |
| 2017/0156859 A1 * | 6/2017 | Chang | A61F 2/2418 |

FOREIGN PATENT DOCUMENTS

| | | |
|---|---|---|
| CN | 101283937 | 10/2008 |
| EP | 1842508 A1 | 10/2007 |
| WO | WO2007/130881 | 11/2007 |
| WO | WO2014/144247 | 9/2014 |

OTHER PUBLICATIONS

PCT/US2016/066313, The International Search Report and the Written Opinion of the International Searching Authority, dated Apr. 6, 2017.

* cited by examiner

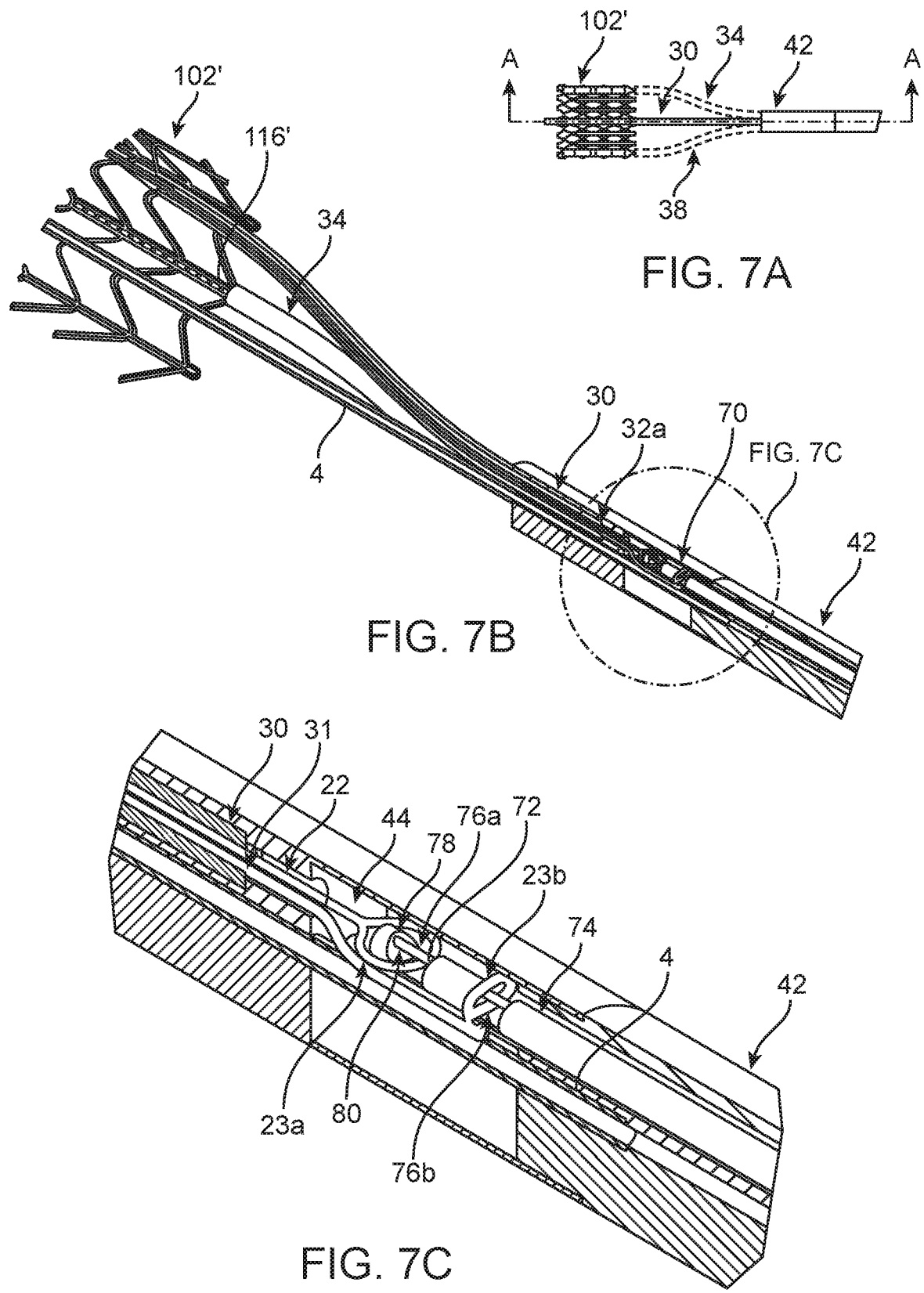

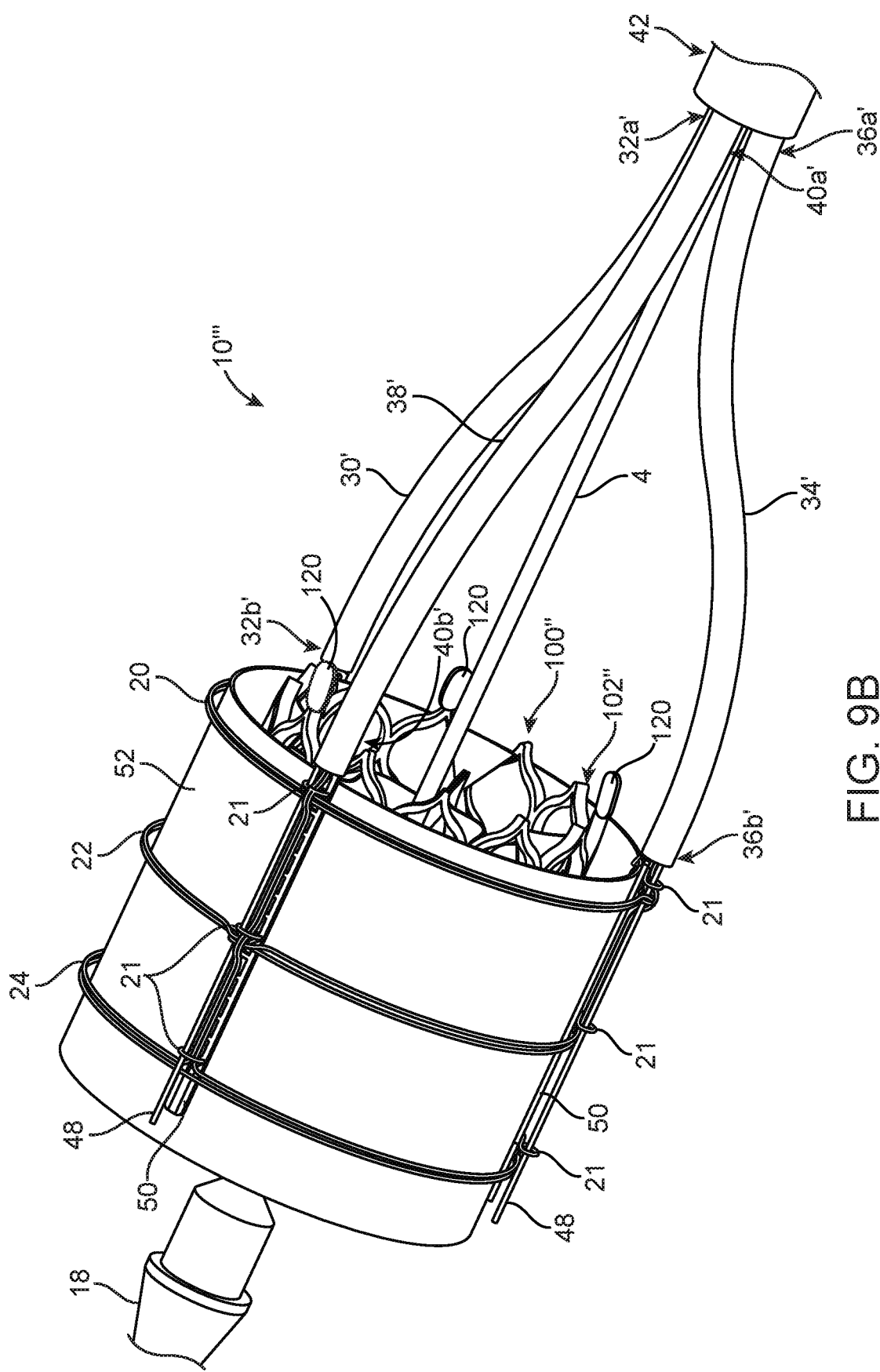

DEVICES AND METHODS FOR TRANSCATHETER VALVE LOADING AND IMPLANTATION

CROSS-REFERENCE TO RELATED APPLICATIONS

This Non-Provisional patent application claims the benefit of the filing dates of U.S. Provisional Patent Application Ser. No. 62/267,200, filed Dec. 14, 2015, entitled "Devices and Methods for Transcatheter Valve Loading and Implantation," which is herein incorporated by reference.

BACKGROUND

The disclosure relates to devices and methods for transcatheter stented prosthetic heart valve loading and implantation.

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of the valve prosthesis on the beating heart, intending to obviate the need for the use of classical sternotomy and cardiopulmonary bypass. In general terms, an expandable prosthetic valve is compressed about or within a catheter, inserted inside a body lumen of the patient, such as the femoral artery, and delivered to a desired location in the heart.

The heart valve prosthesis employed with catheter-based, or transcatheter, procedures generally includes an expandable multi-level frame or stent that supports a valve structure having a plurality of leaflets. The frame can be contracted during percutaneous transluminal delivery, and expanded upon deployment at or within the native valve. One type of valve stent can be initially provided in an expanded or uncrimped condition, then crimped or compressed about a balloon portion of a catheter. The balloon is subsequently inflated to expand and deploy the prosthetic heart valve. With other prosthetic heart valve designs, the stent frame is formed to be self-expanding. With these delivery devices, the valved stent is crimped down to a desired size and held in that compressed state within a sheath for translumenal delivery. Retracting the sheath from this valved stent allows the stent to self-expand to a larger diameter, fixating at the native valve site. In more general terms, then, once the prosthetic valve is positioned at the treatment site, for instance within an incompetent native valve, the stent frame structure may be expanded to hold the prosthetic valve firmly in place. One example of a prosthetic valve is disclosed in U.S. Pat. No. 5,957,949 to Leonhardt et al., which is incorporated by reference herein in its entirety.

The actual shape and configuration of any particular transcatheter stented prosthetic heart valve is dependent, at least to some extent, upon the valve being replaced or repaired (e.g., mitral valve, tricuspid valve, aortic valve, or pulmonary valve). The stent frame must oftentimes provide and maintain (e.g., elevated hoop strength and resistance to radially compressive forces) a relatively complex shape in order to achieve desired fixation with the corresponding native anatomy. Taken in combination, these design features can give rise to delivery obstacles. For example, when compressed and constrained within the delivery device's outer sheath capsule, a self-expanding stent frame will exert significant radial forces on the capsule. Thus, the capsule must have a robust construction, capable of statically resisting the applied force. However, the capsule, as well as other portions of the outer sheath, must also be sufficiently flexible to traverse the tortuous path leading to the native valve annulus site. As a point of reference, the preferred delivery approach oftentimes includes one or more significant bends or turns. In many instances, the native anatomy creates the "tight" or small radius of curvature bends; as the capsule (or other components of the delivery device) comes into atraumatic contact with the native anatomy, the native anatomy naturally assists in "forcing" the outer sheath (including the capsule) to the necessary shape. A retrograde approach to the aortic valve is but one example, where contact with the native anatomy assists in directing the delivery device about the significant curvature of the aortic arch.

The present disclosure addresses problems and limitations with the related art.

SUMMARY

The present disclosure relates to numerous delivery devices and methods for transcatheter stented prosthetic heart valve ("prosthetic valve") loading, delivery and implantation. Such delivery devices can include an optional outer delivery sheath assembly, an inner shaft assembly and a handle assembly. The delivery device provides a loaded delivery state in which the prosthetic valve is loaded and compressed over the inner shaft assembly. The compression on the prosthetic valve can be adjusted with one or more sutures. The delivery device can be manipulated to permit the prosthetic valve to self-expand and partially release from the inner shaft assembly.

Some aspects of the disclosure relate to suture routing methods in which one or more sutures are positioned around a stent frame of a stented prosthetic heart valve. In various embodiments, each suture spans approximately one third of a circumference of the stent frame. In other embodiments, each suture can span generally the entire circumference of the stent frame. In even further embodiments, certain sutures can span generally one-third of the circumference of the stent frame while others span the remaining two-thirds of the circumference of the stent frame. In various embodiments, the sutures are attached to a respective release mechanism. Such delivery devices provide for independent adjustment of each suture (i.e. expanding and contracting of the prosthetic valve) prior to the suture being released by the release mechanism. Alternately, sutures can be connected to shared release mechanisms. In certain embodiments, the release mechanism includes a release pin that can be selectively withdrawn to disengage from one or more sutures to release said sutures from the stent frame after expansion of the stent frame at the defective native heart valve. After the sutures are released from the stent frame, the delivery device can be withdrawn from the patient.

BRIEF DESCRIPTION OF THE DRAWINGS

FIG. 7A is a partial, side view of one delivery device having a release mechanism positioned within a shaft of the delivery device.

FIG. 7B is a partial, cross-sectional view of the delivery device of FIG. 7A as viewed along line A-A illustrating the release mechanism.

FIG. 7C is an enlarged view of Section 7C of FIG. 7B.

FIG. 9B is an assembled, perspective view of the delivery device of FIG. 9A.

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. As used herein with reference to a stented prosthetic heart valve, the terms "distal" and "outflow" are understood to mean downstream to the direction of blood flow, and the terms "proximal" or "inflow" are understood to mean upstream to the direction of blood flow. Although the present disclosure has been described with reference to preferred embodiments, workers skilled in the art will recognize that changes can be made in form and detail without departing from the spirit and scope of the present disclosure.

Figure 1:
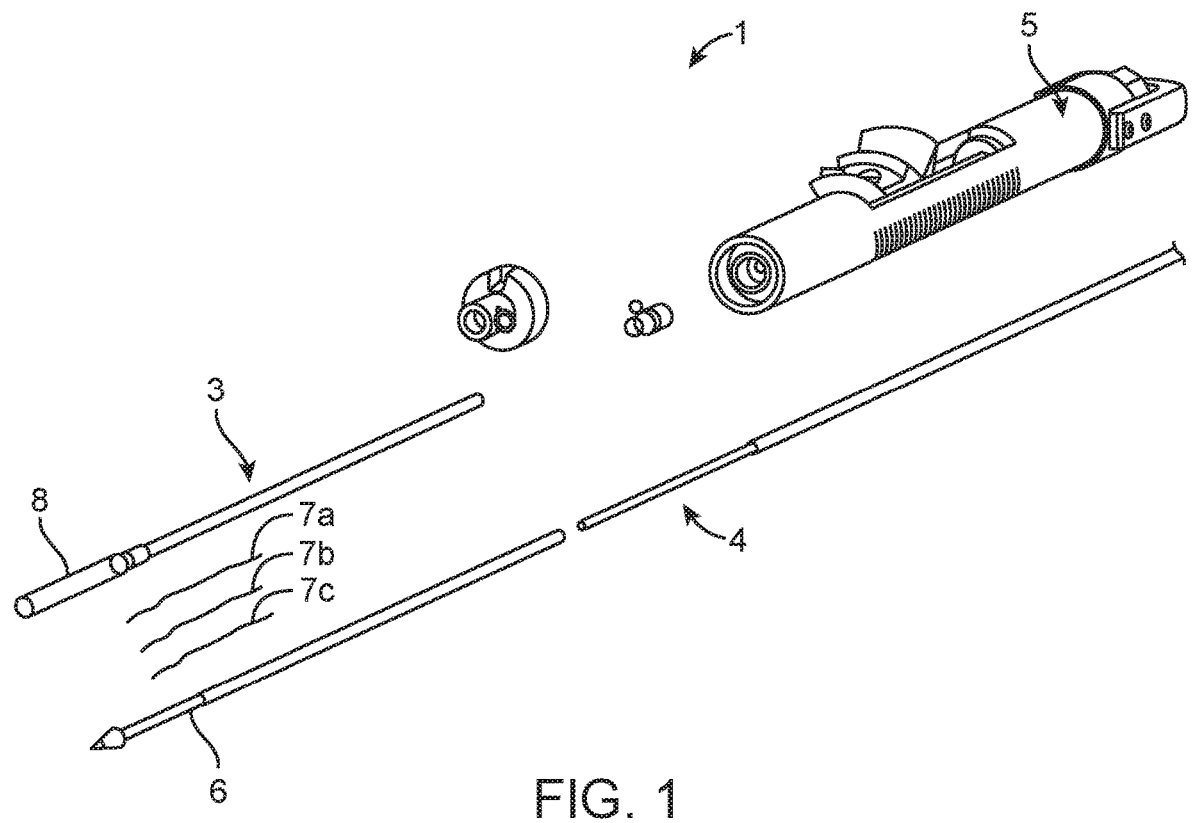
FIG. 1 is a perspective view of a delivery device for delivering a stented prosthetic heart valve.
Figure 2A:
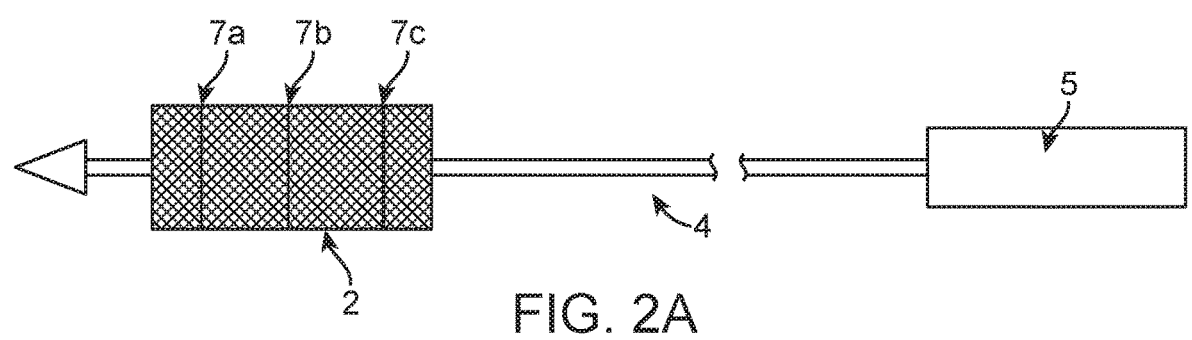
FIG. 2A is a partial, schematic illustration of the delivery device of FIG. 1 having a stented prosthetic heart valve positioned over an inner shaft assembly; the stented prosthetic heart valve shown in an expanded state.
Figure 2B:
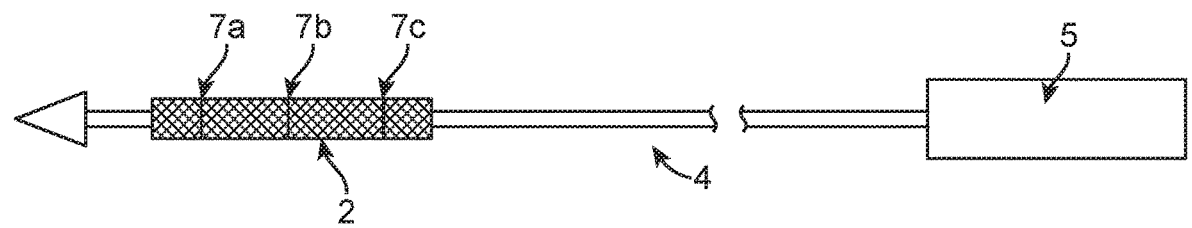
FIG. 2B is a schematic illustration of the delivery device of FIG. 2A having a stented prosthetic heart valve positioned over the inner shaft assembly; a plurality of sutures compressing the prosthetic heart valve into a compressed state.

As described below, aspects of the present disclosure relate to delivery devices utilizing one or more sutures to retain the stented prosthetic heart valve ("prosthetic valve") in a compressed state during delivery to a target site. The suture related features of the present disclosure are useful with a variety of different delivery devices configurations. By way of background, general components of one non-limiting example of a delivery device 1 with which the present disclosures are useful are illustrated in FIGS. 1-2B. The delivery device 1 is arranged and configured for percutaneously delivering a prosthetic valve 2 to a patient's defective heart valve. The delivery device 1 includes an optional outer delivery sheath assembly 3, an inner shaft assembly 4, and a handle assembly 5. One or more sutures 7a-7c (schematically depicted) are provided, and can be considered part of the delivery device 1 in some embodiments or as part of the prosthetic valve 2 in other embodiments. The delivery device 1 provides a loaded delivery state in which the prosthetic valve 2 is loaded over the inner shaft assembly 4 and is compressively retained on a spindle 6 or the like by the sutures 7a-7c. As is schematically illustrated in FIGS. 2A-2B, the compression on the prosthetic valve 2 is adjustable with one or more sutures 7a-c. Once the loaded and compressed prosthetic valve 2 is located at a target site, tension in the sutures 7a-7c is lessened or released to permit the prosthetic valve 2 to self-expand, partially releasing and ultimately fully deploying the prosthetic valve 2 from the inner shaft assembly 4. In the illustrated embodiment, the optional delivery sheath assembly 3, where provided, includes a capsule 8, selectively disposed over the prosthetic valve 2 that assists in constraining the prosthetic valve 2 in the loaded or compressed state and can be retracted by the handle assembly 5 to expose the prosthetic valve 2. The present disclosure focuses on numerous devices and methods for prosthetic valve loading and implantation using a delivery device, such as the delivery device 1. Such delivery devices utilize sutures for adjustably compressing and releasing said compression on the prosthetic valve and the disclosure further focuses on delivery device configurations that reduce suture tangling.

As referred to herein, prosthetic valves useful with the various devices and methods of the present disclosure may assume a wide variety of configurations, such as a bioprosthetic heart valve having tissue leaflets or a synthetic heart valve having polymeric, metallic or tissue-engineered leaflets, and can be specifically configured for replacing valves of the human heart. The prosthetic valves of the present disclosure may be self-expandable, balloon expandable and/or mechanically expandable or combinations thereof. In general terms, the prosthetic valves of the present disclosure include a stent or stent frame having an internal lumen maintaining a valve structure (tissue or synthetic), with the stent frame having a normal, expanded condition or arrangement and collapsible to a compressed condition or arrangement for loading within the delivery device. For example, the stents or stent frames are support structures that comprise a number of struts or wire segments arranged relative to each other to provide a desired compressibility and strength to the prosthetic valve. The struts or wire segments are arranged such that they are capable of self-transitioning from, or being forced from, a compressed or collapsed condition to a normal, radially expanded condition. The struts or wire segments can be formed from a shape memory material, such as a nickel titanium alloy (e.g., Nitinol™). The stent frame can be laser-cut from a single piece of material, or can be assembled from a number of discrete components.

Figure 3:
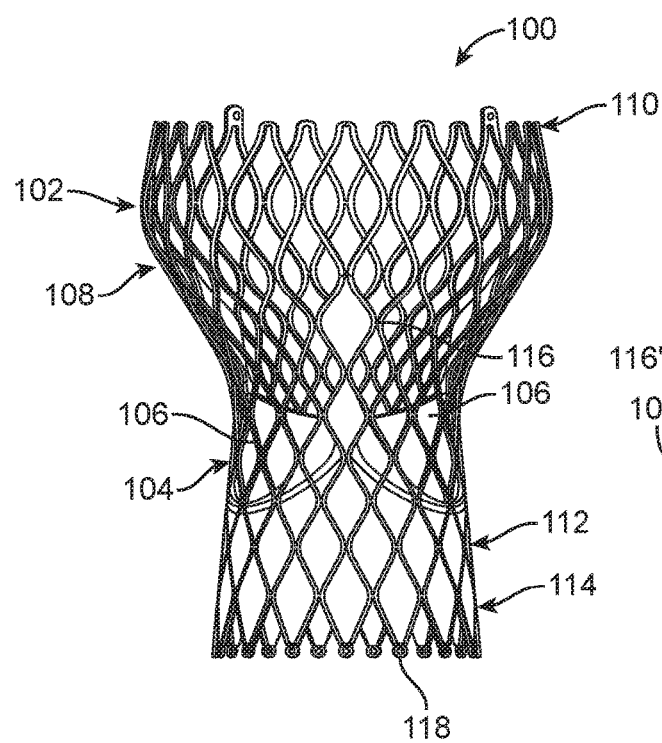
FIG. 3 is a front view of a stented prosthetic heart valve that can be used with the delivery devices disclosed herein.

One simplified, non-limiting example of a prosthetic valve 100 is illustrated in FIG. 3. As a point of reference, the prosthetic valve 100 is shown in a normal or expanded state in the view of FIG. 3. The prosthetic valve 100 includes a stent or stent frame 102 and a valve structure 104. The stent frame 102 can assume any of the forms mentioned above, and is generally constructed to be self-expandable from the compressed state to the normal, expanded state.

The valve structure 104 of the prosthetic valve 100 can assume a variety of forms, and can be formed, for example, from one or more biocompatible synthetic materials, synthetic polymers, autograft tissue, homograft tissue, xenograft tissue, or one or more other suitable materials. In some embodiments, the valve structure 104 can be formed, for example, from bovine, porcine, equine, ovine and/or other suitable animal tissues. In some embodiments, the valve structure 104 can be formed, for example, from heart valve tissue, pericardium, and/or other suitable tissue. In some embodiments, the valve structure 104 can include or form one or more leaflets 106. For example, the valve structure 104 can be in the form of a tri-leaflet bovine pericardium valve, a bi-leaflet valve, or another suitable valve.

In some prosthetic valve constructions, such as that of FIG. 3, the valve structure 104 can comprise two or three leaflets that are fastened together at enlarged lateral end regions to form commissural joints, with the unattached edges forming coaptation edges of the valve structure 104. The leaflets 106 can be fastened to a skirt that in turn is attached to the stent frame 102. The prosthetic valve 100 includes an outflow portion 108 corresponding to a first or outflow end 110 (forcing out fluid) of the prosthetic valve 100. The opposite end of the prosthetic valve 100 can define an inflow portion 112 corresponding to a second or inflow end 114 (receiving fluid). As shown, the stent frame 102 can have a lattice or cell-like structure, and optionally forms or provides posts 116 corresponding with commissures of the valve structure 104 as well as eyelets 118 (or other shapes) at the outflow and inflow ends 110, 114. If provided, the posts 116 are spaced equally around frame 102 (only one post 116 is clearly visible in FIG. 3).

Figure 4:
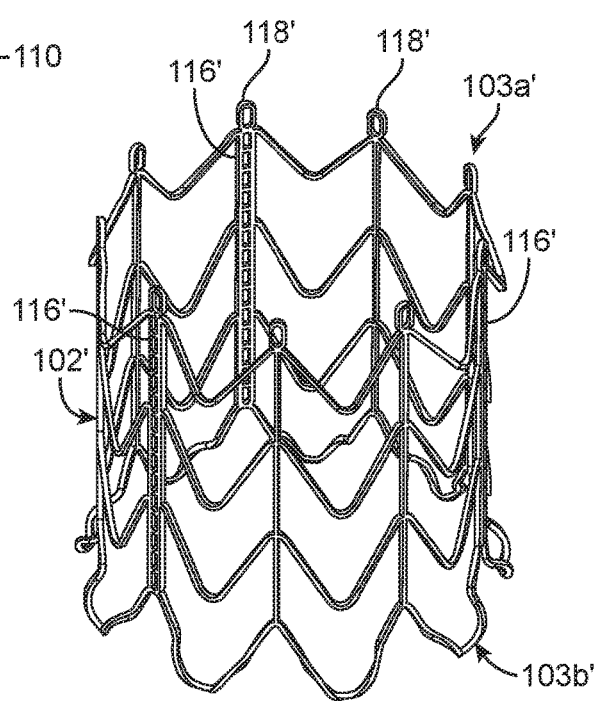
FIG. 4 is a perspective view of an alternate stented prosthetic heart valve frame configuration.

One alternative stent frame 102' is illustrated in FIG. 4. The stent frame 102' is shown in an expanded state and has a proximal end 103a' and a distal end 103b' as well as a plurality of slotted posts 116' and eyelets 118' spaced equally around the stent frame 102'. It will be understood that the alternate stent frame 102' can replace stent frame 102 of FIG. 3.

Figure 5A:
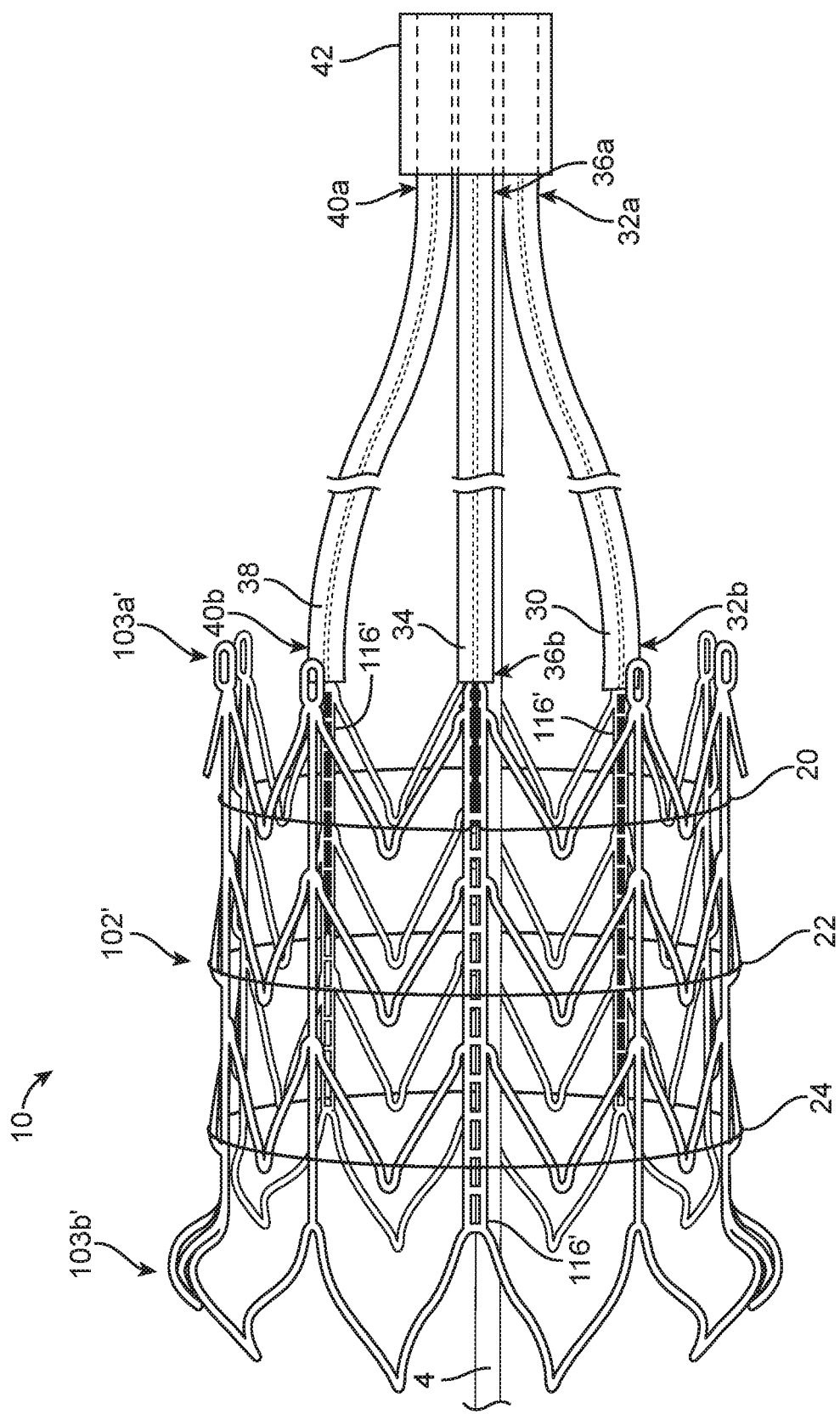
FIG. 5A is a partial, side view of one delivery device for delivering a stented prosthetic heart valve (only the stent frame of the stented prosthetic heart valve is shown for clarity).

Select components of one delivery device 10 are shown in FIG. 5A relative to a prosthetic valve during an initial stage of loading the prosthetic valve to the delivery device 10 (only the stent frame 102' is shown for ease of illustration). In general terms, the delivery device includes an inner shaft 4, a guide shaft 42, first, second and third tubes 30, 34, 38, and first, second and third sutures 20, 22, 24. The inner shaft 4 extends from the guide shaft 42 and carries a dilator similar to the dilator 18 of FIG. 1. A guide wire lumen is formed through the dilator, inner shaft 4 and guide shaft 42, and is sized to slidably receive a guidewire that can otherwise be utilized with the delivery device 10. To facilitate delivery of the prosthetic valve to a defective native heart valve, the sutures 20, 22, 24 apply tension to compress the stent frame 102' to place the stent frame 102' and thus, the prosthetic valve, in a compressed state, reducing its diameter so that the prosthetic valve can pass through a patient's vascular system.

Figure 5B:
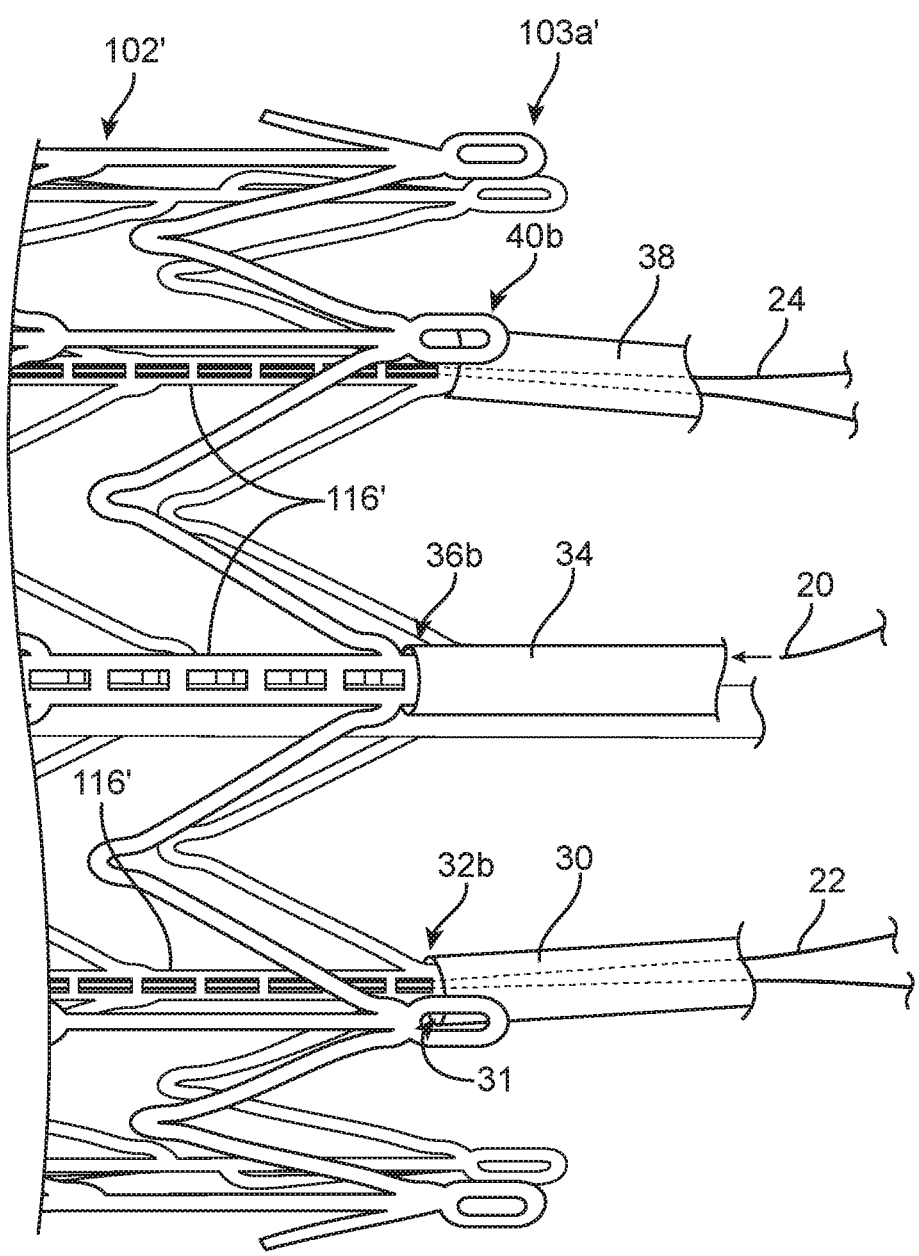
FIGS. 5B-5I are partial, schematic views of the delivery device of FIG. 5A illustrating one method and configuration of suture routing.
Figure 5C:
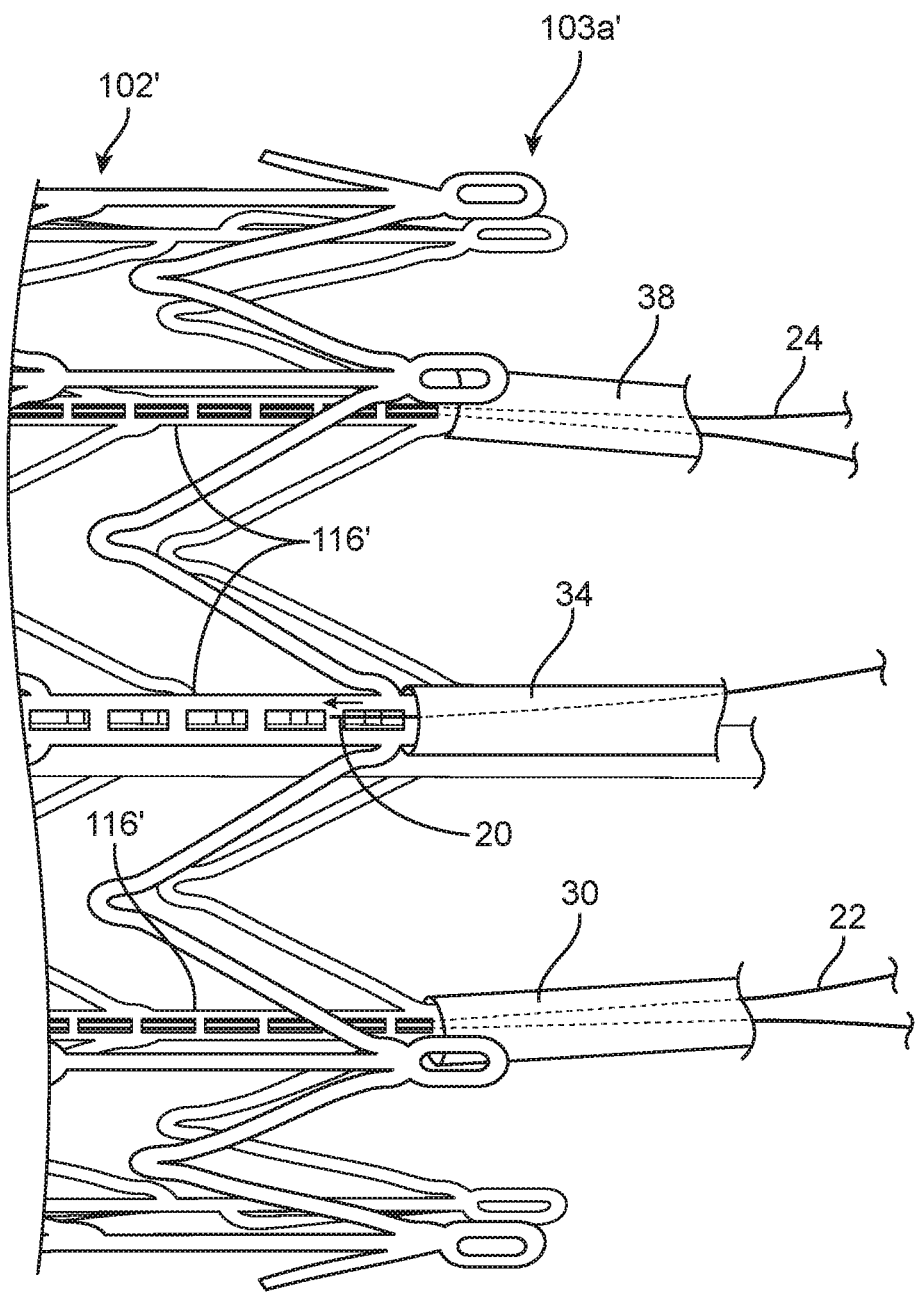
Figure 5D:
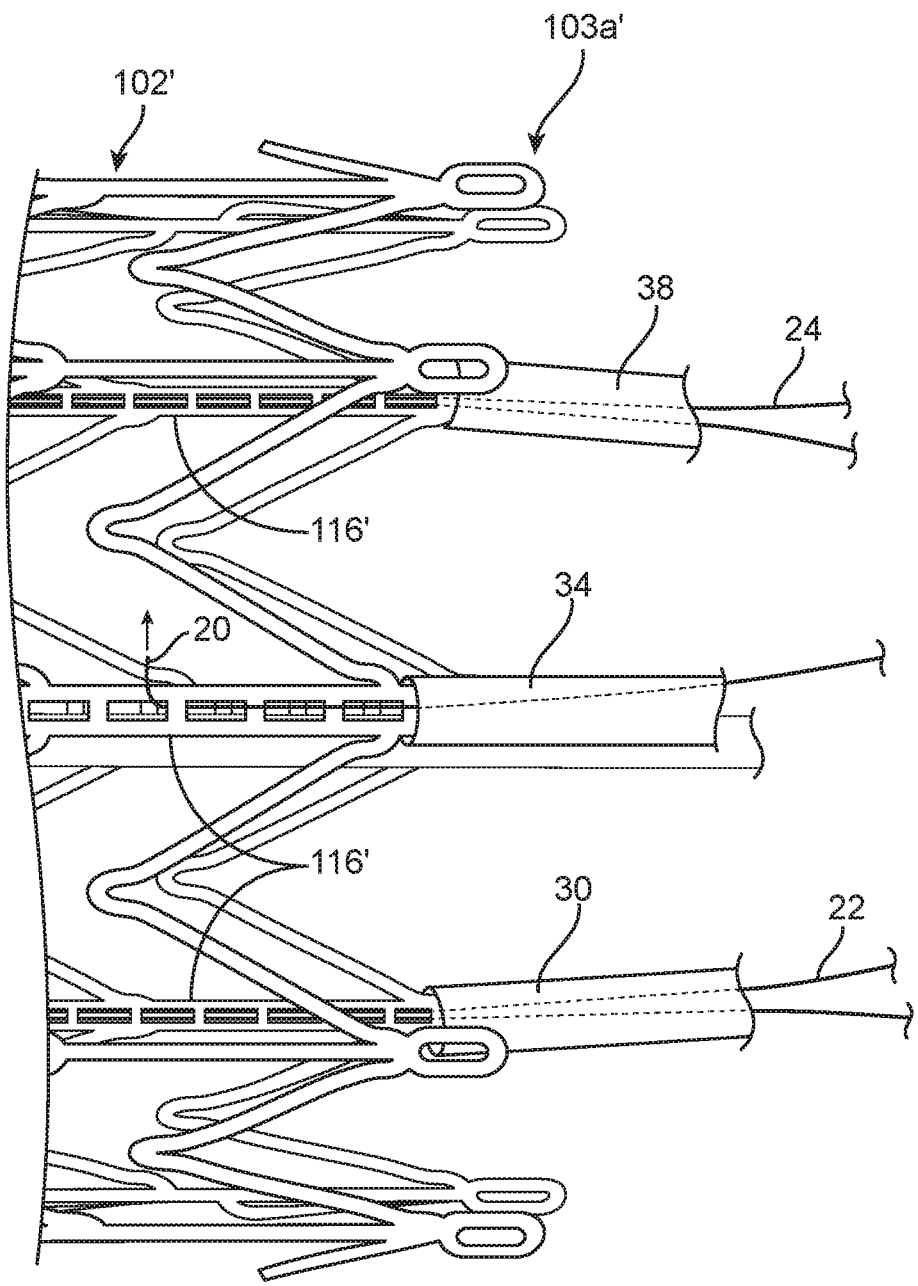
Figure 5E:
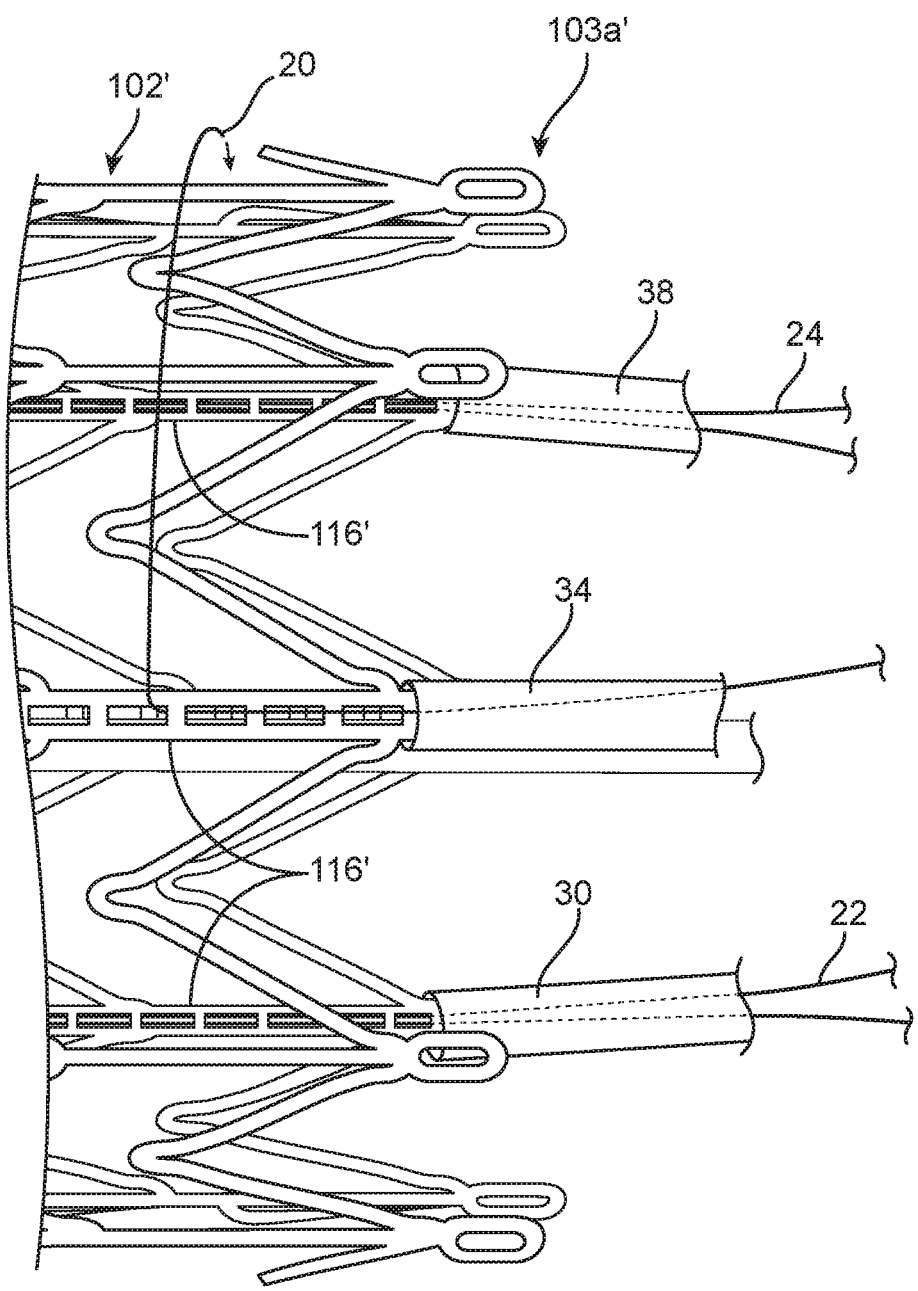
Figure 5F:
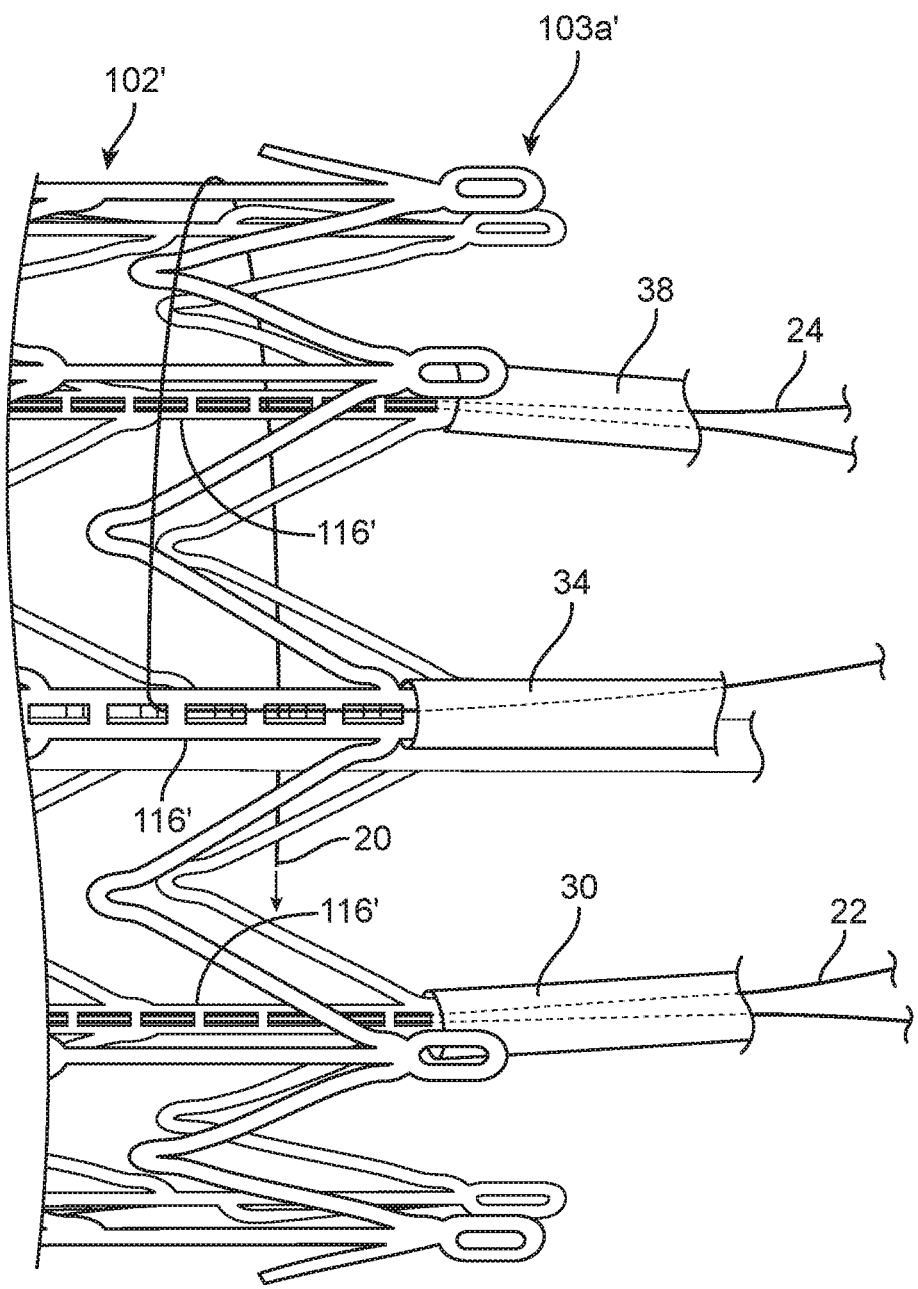
Figure 5G:
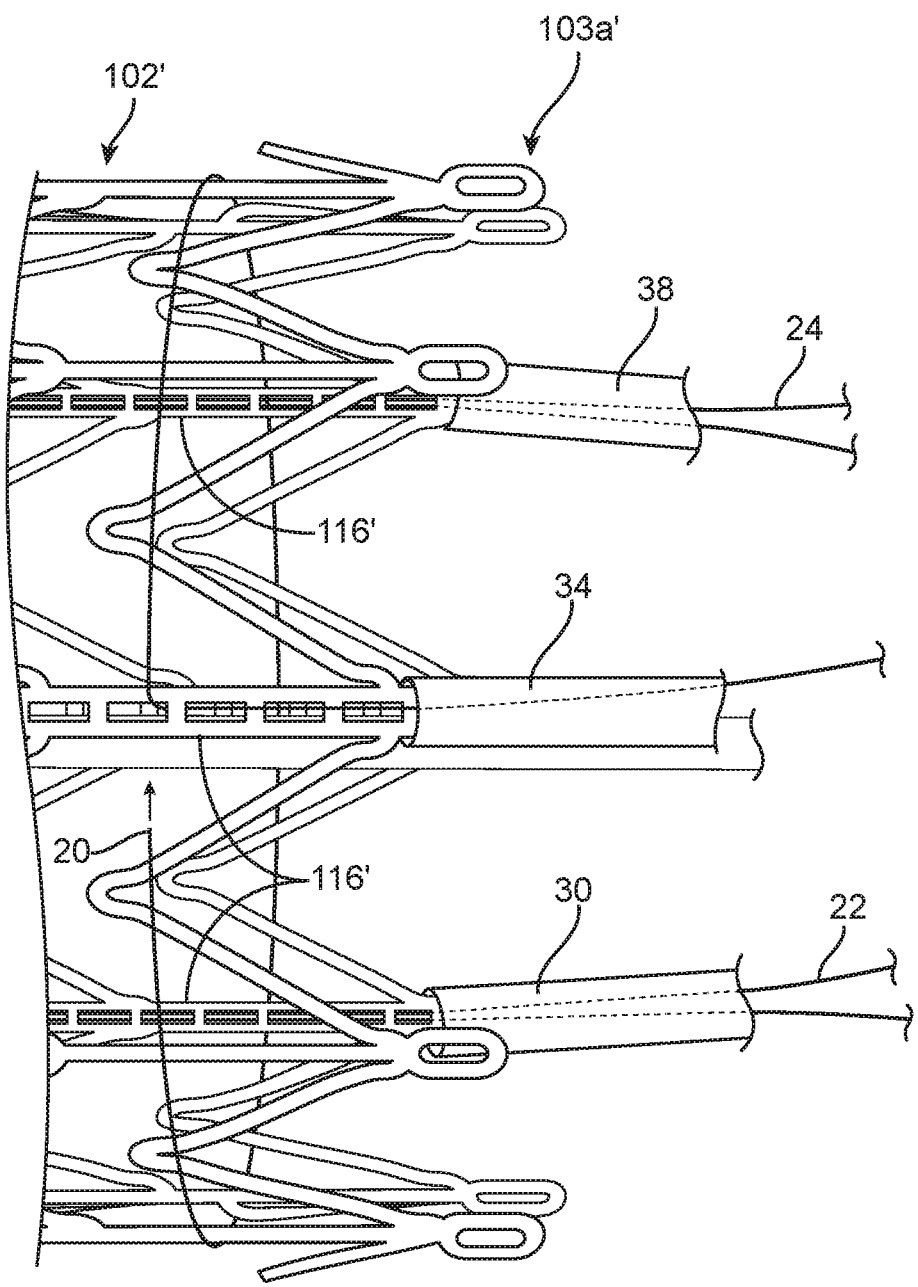
Figure 5H:
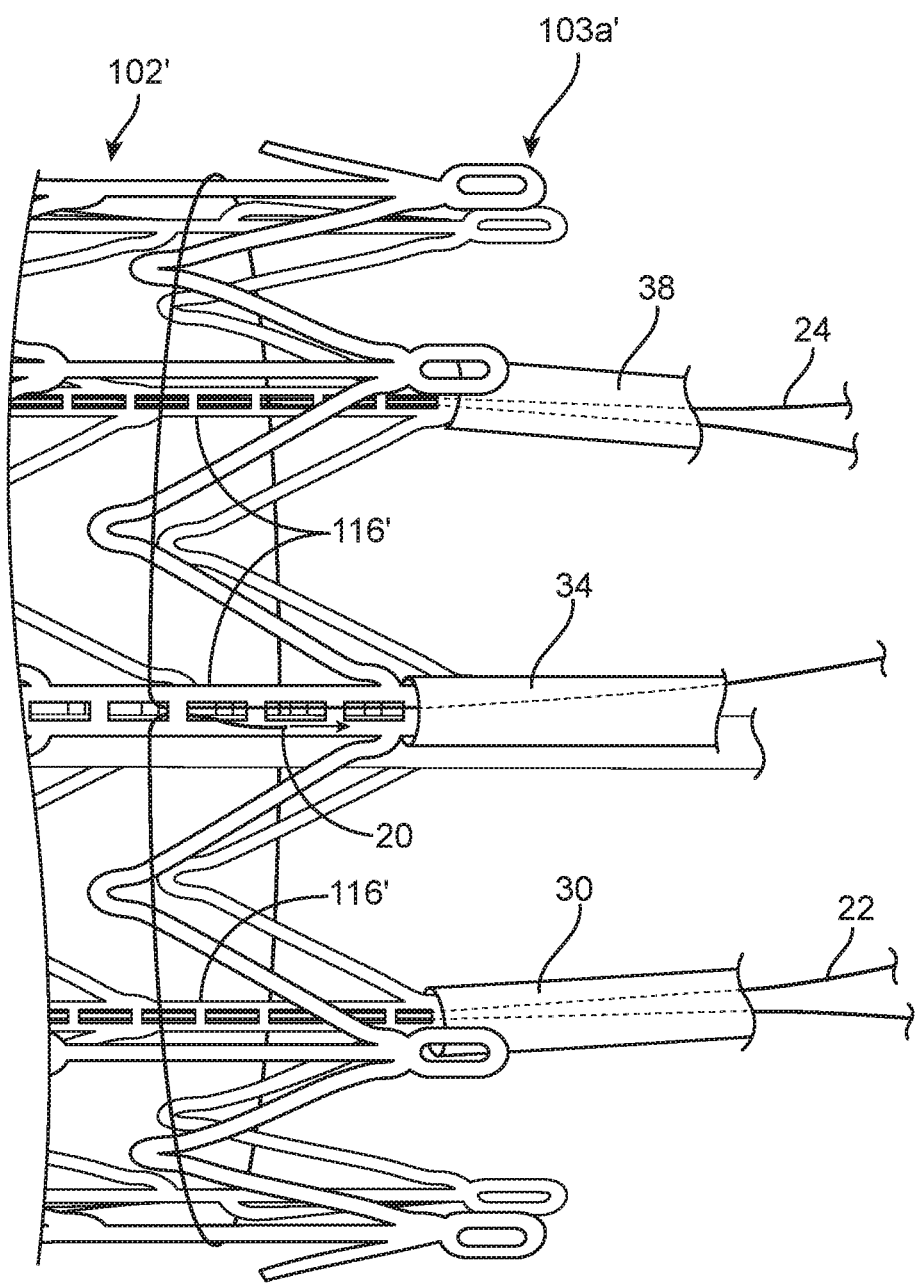
Figure 5I:
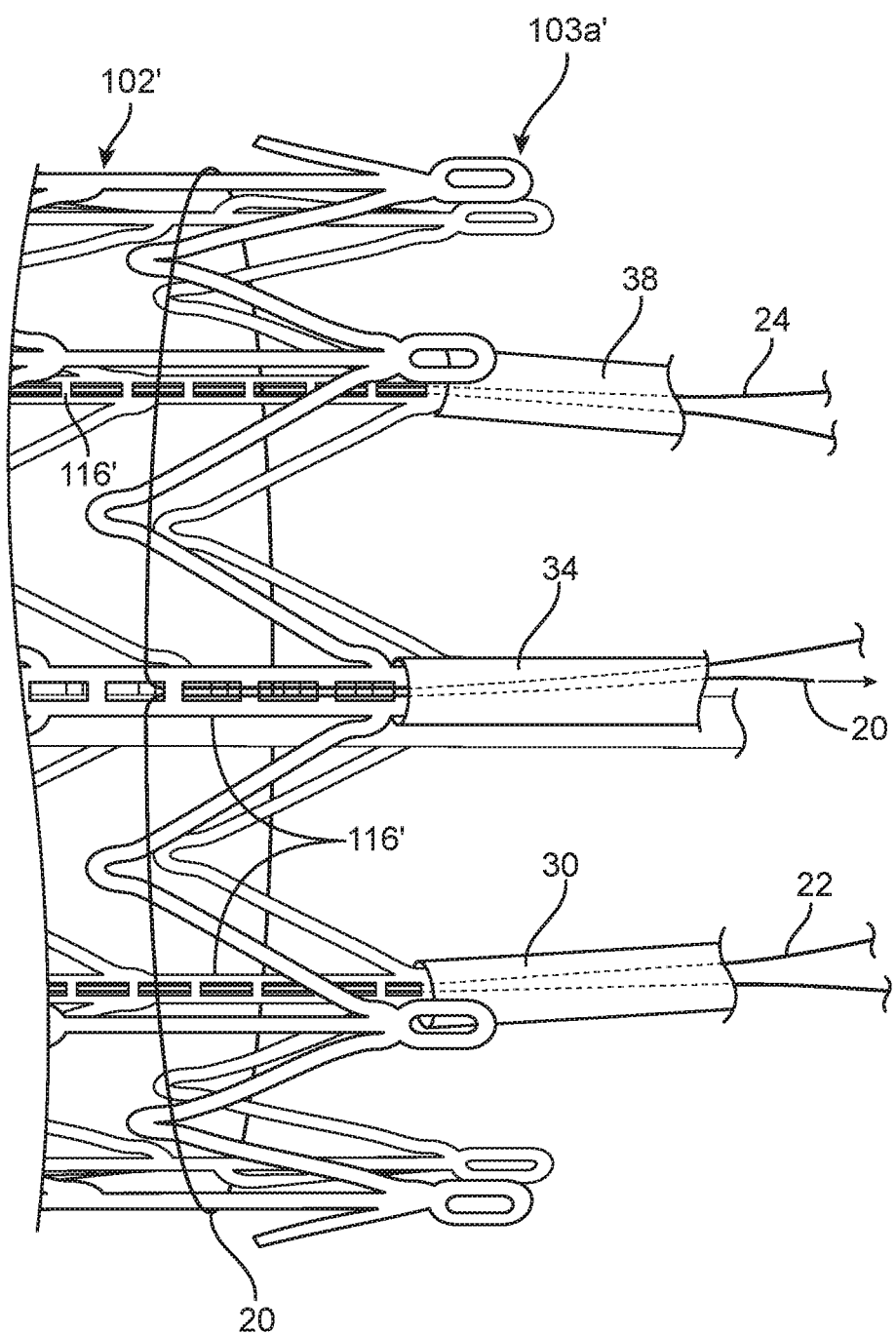
Figure 8A:
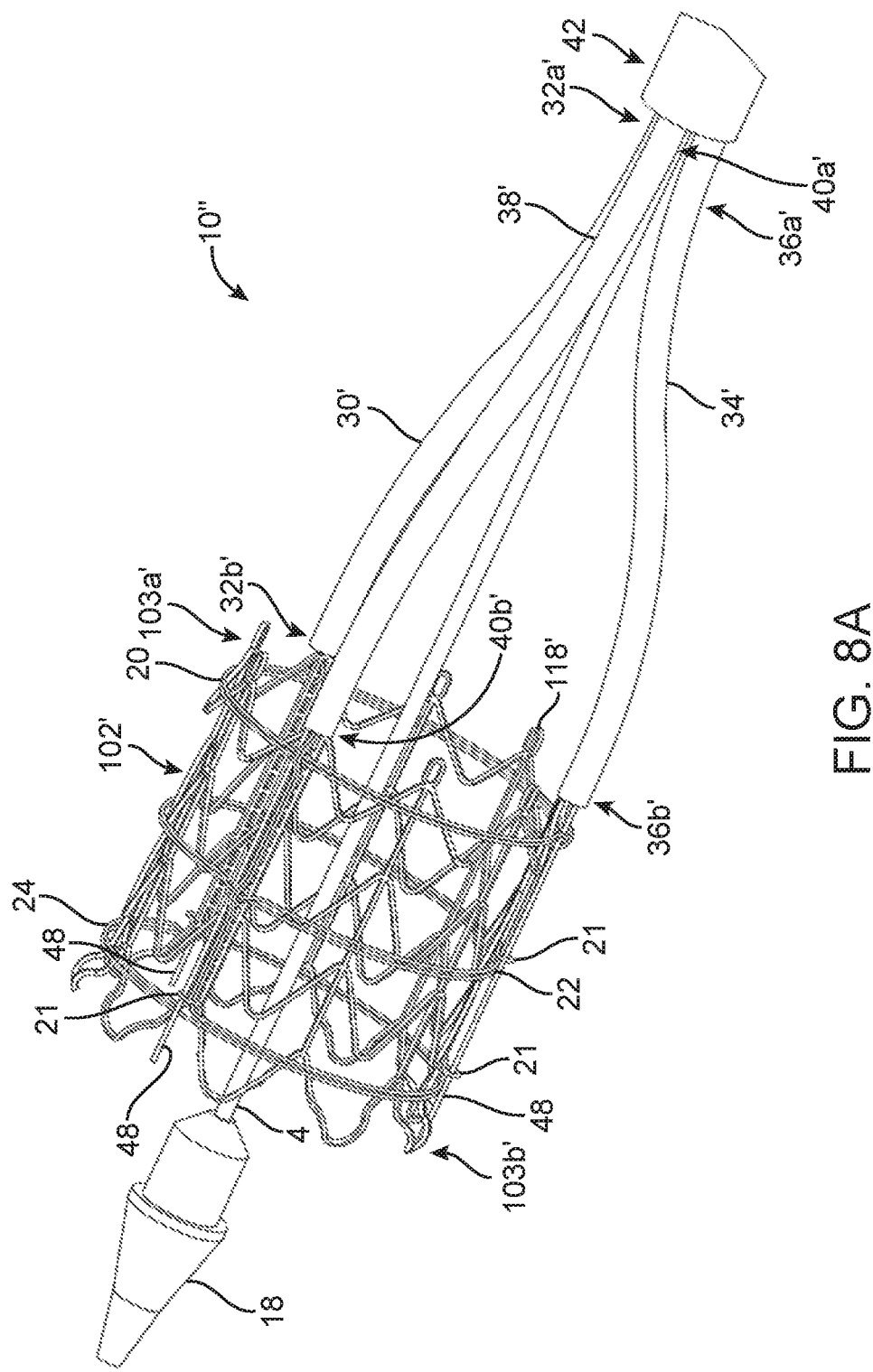
FIG. 8A is a partial, perspective view one delivery device, similar to that of FIGS. 1-2B and 5A-6L for delivering a stented prosthetic heart valve (only the stent frame of the stented prosthetic heart valve is shown for clarity).
Figure 8B:
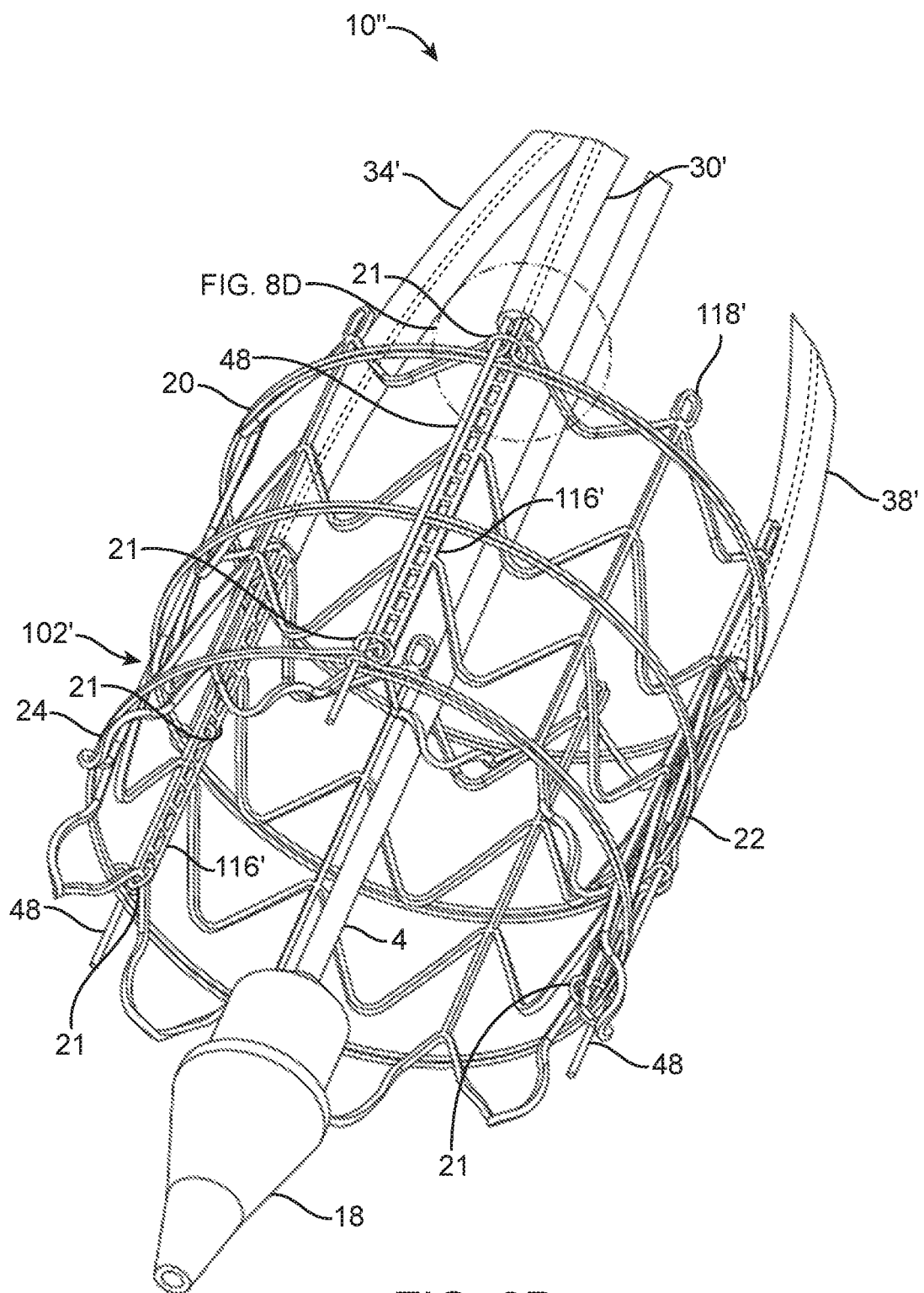
FIG. 8B is a partial, perspective view of the delivery device of FIG. 8A having the stent frame loaded thereto with a plurality of sutures.
Figure 8C:
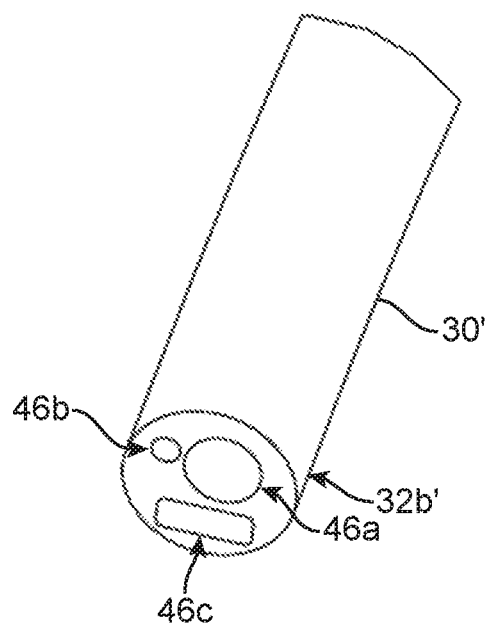
FIG. 8C is an enlarged view of Section 8C of FIG. 8B.
Figure 8D:
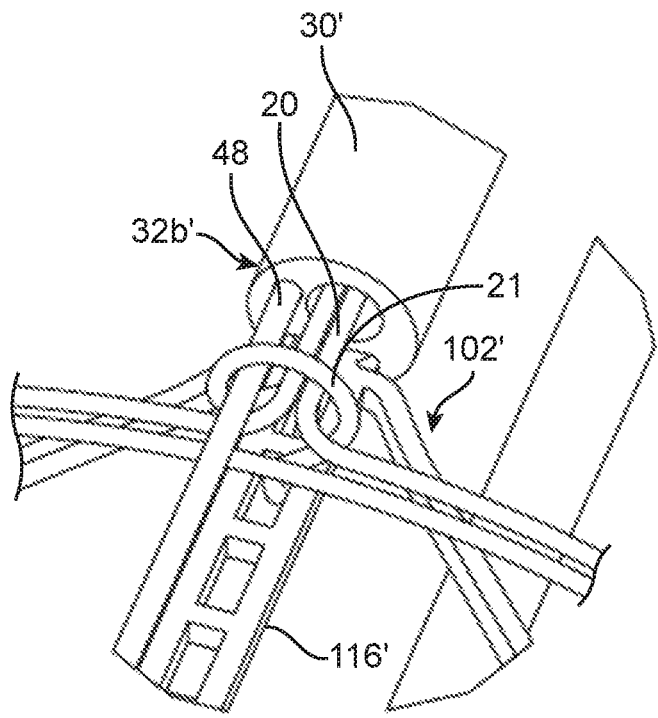
FIG. 8D is a partial, perspective view of a distal end of a tube of the delivery device of FIGS. 8A-8C.

In general terms, the sutures 20, 22, 24 are routed through one or more of the tubes 30, 34, 38 and about at least a portion of the stent frame 102'. The first, second and third tubes 30, 34, 38 each include a proximal end 32a, 36a, 40a and a distal end 32b, 36b, 40b. The proximal ends 32a, 36a, 40a are connected to and extend distally from the guide shaft 42 that is interconnected to a handle assembly (not shown), such as the handle assembly 5 of FIG. 1. The handle assembly is configured to provide and release tension in the sutures 20, 22, 24 (otherwise routed to the tubes 30, 34, 38) to correspondingly compress the stent frame 102' and release said tension to allow the stent frame 102' to expand. The distal ends 32b, 36b, 40b of tubes 30, 34, 38 may have a short section where the diameter is slightly larger to receive the eyelets 118' to engage the stent frame 102'. Also, there may be a separate blind pocket at the distal ends of the tubes as shown in FIG. 8C. Alternatively, the distal ends 32b, 36b, 40b can receive a finger, paddle or other feature of the stent frame 102'. The tubes 30, 34, 38 are made of a semi-rigid material, such as polyether ether ketone (PEEK), for example. The tubes 30, 34, 38 are semi-rigid to provide a level of flexibility when the stent frame 102' is in an expanded state but rigid enough such that the prosthetic valve can be guided or "pushed" through a patient's vasculature to the defective valve and also to resist compression which could affect placement accuracy. The tubes 30, 34, 38 are generally hollow and each include one or more lumens 31 for the routing of at least one of the sutures 20, 22, 24 (only lumen 31 of first tube 30 is labeled in FIG. 5B for ease of illustration).

In one example embodiment, the delivery device 10 includes a single proximal suture 20, a single intermediate suture 22 and a single distal suture 24, each suture extending from the distal end 32b, 36b, 40b of one respective tube 30, 34, 38 to the stent frame 102'. Each suture 20, 22, 24 is woven around generally the entire circumference of the stent frame 102' and then back down through the respective tube 30, 34, 38 from which the suture 20, 22, 24 originated. Though not shown, stay sutures similar to element 21 of FIGS. 8A-8D may be located around the perimeter of the frame to help the sutures track where desired For example, as generally illustrated in FIGS. 5B-5I, the proximal suture 20 is routed from the proximal end 36a of the second tube 34 to the distal end 36b of the second tube 34, then woven around the circumference of the proximal end 130a' of the stent frame 102', and then threaded back through the second tube 34 to the proximal end 36a of the second tube 34. The intermediate and distal sutures 22, 24 are routed in a similar manner. The intermediate suture 22 is threaded through the first tube 30 from the proximal end 32a to the distal end 32b, then around the approximate center of the stent frame 102' and then back down the first tube 30 to the proximal end 32a of the first tube 30. The distal suture 24 is similarly threaded through the proximal end 40a of the third tube 38 to the distal end 40b, then around the distal end 103b' of the stent frame 102' and then back down through the distal end 40b of the third tube 38 to the proximal end 40a of the third tube 38. Sutures 20, 22 and 24 can be threaded around the circumference of the stent frame 102' in the same or alternating directions. Each suture 20, 22, 24 can be releasably secured to a release mechanism 70 located within a lumen 44 of the shaft 42 as is generally illustrated in FIGS. 7A-7C and discussed below, for example. Once tension in the sutures 20, 22 and 24 is released by the release mechanism or other means, the stent frame 102' can expand to the expanded state either via a natural bias or other methods disclosed herein. In the present embodiment, tension in each suture 20, 22, 24 can be independently released to allow only a portion of the valve to self-expand. Once all of the sutures 20, 22, 24 are released, the sutures 20, 22 and 24 and the delivery device can be retracted and removed from the patient. This device 10 can be used with or without a capsule (not shown), such as the capsule 8 of FIG. 1.

Figure 6A:
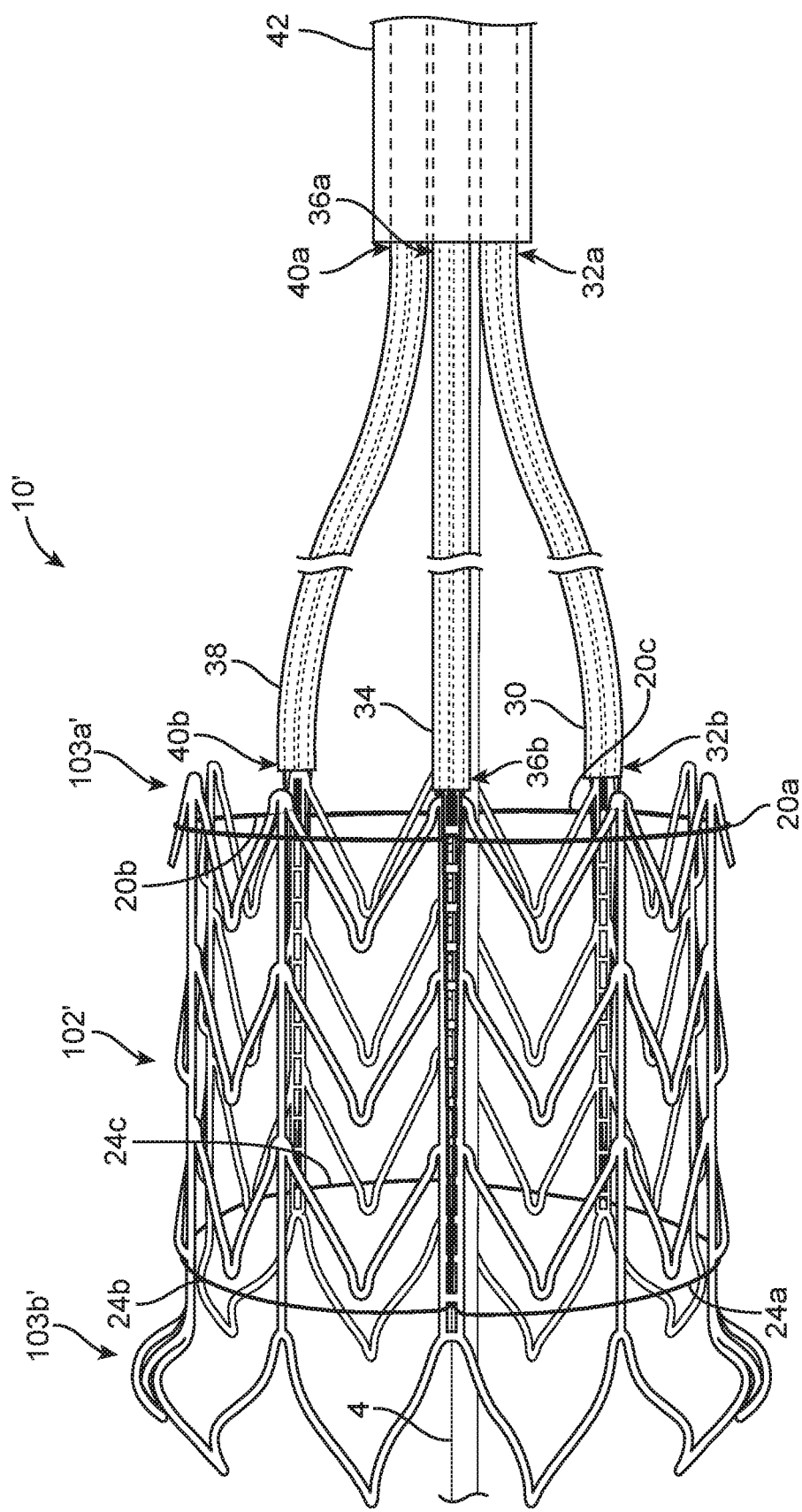
FIG. 6A is a partial, schematic view of a second delivery device illustrating a second method and configuration of suture routing.
Figure 6B:
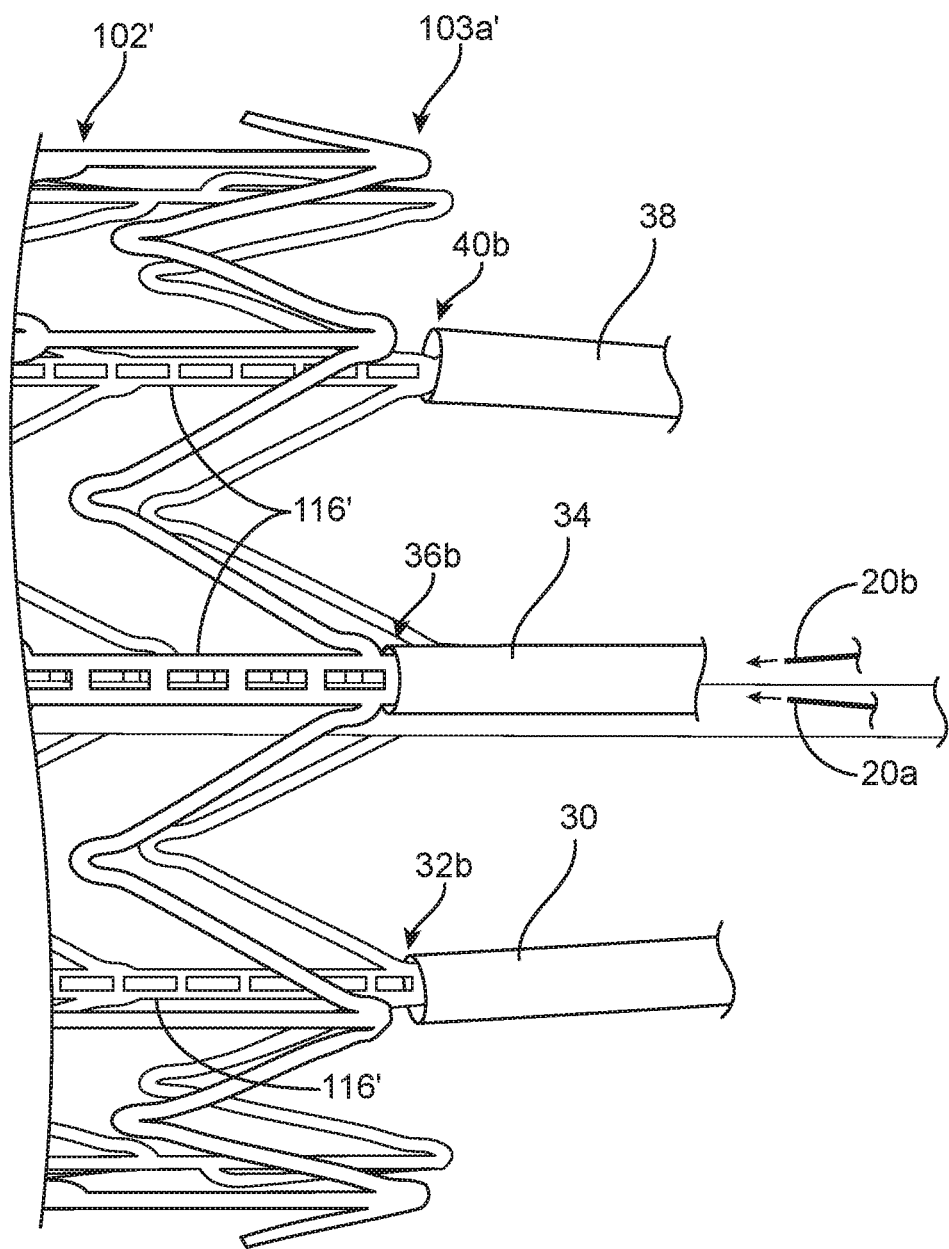
FIGS. 6B-6L are partial, schematic views of the delivery device of FIG. 6A illustrating one method and configuration of suture routing.
Figure 6C:
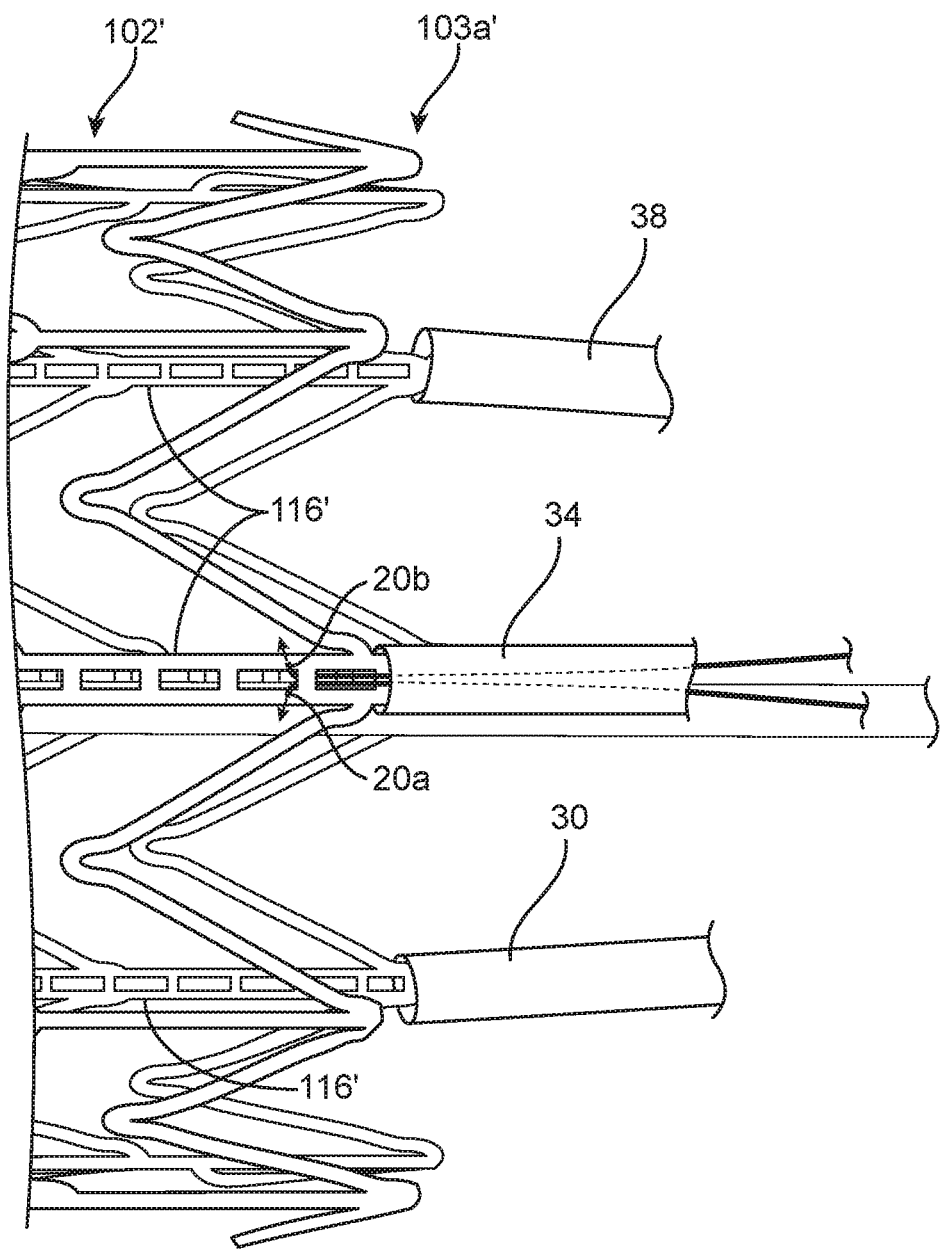
Figure 6D:
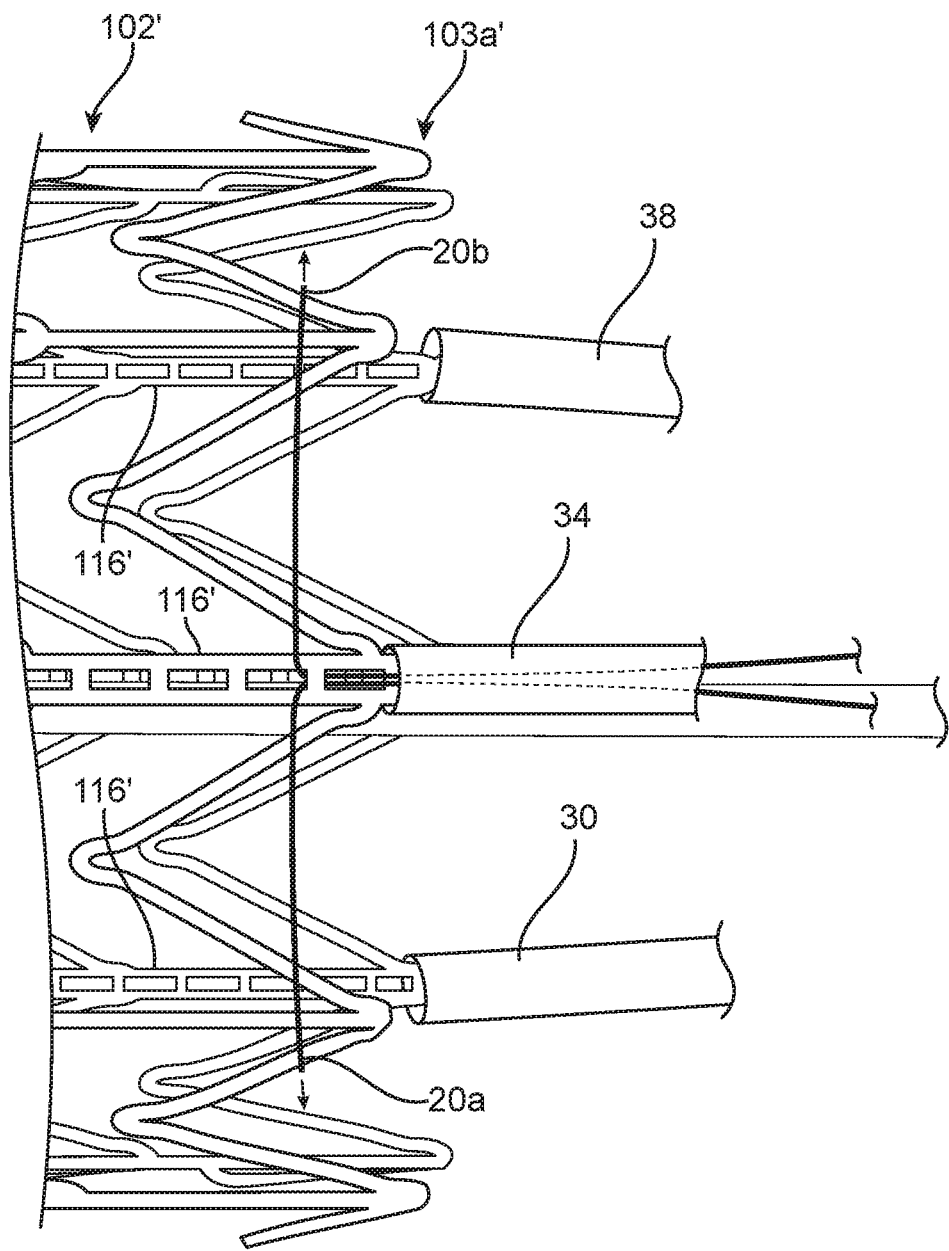
Figure 6E:
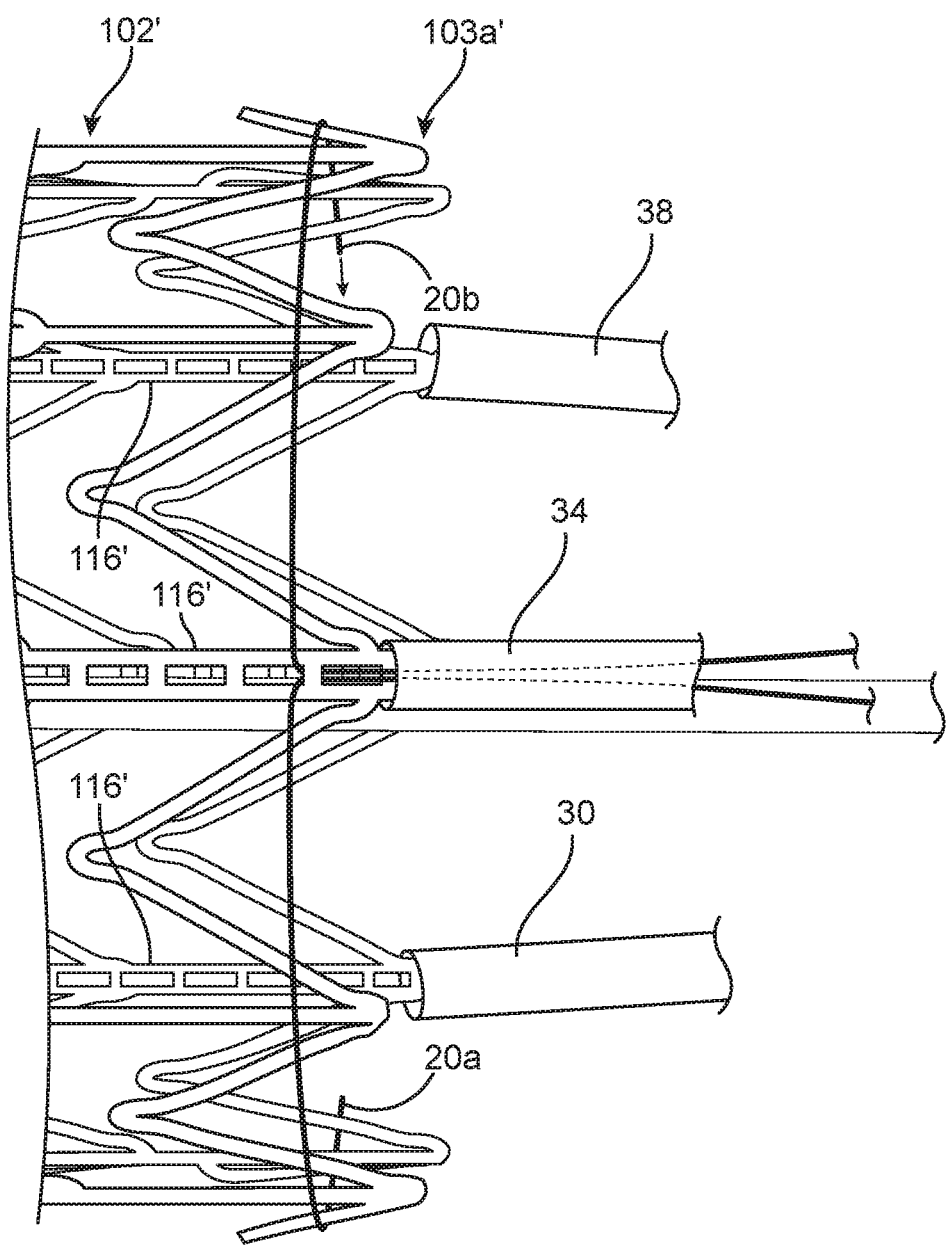
Figure 6F:
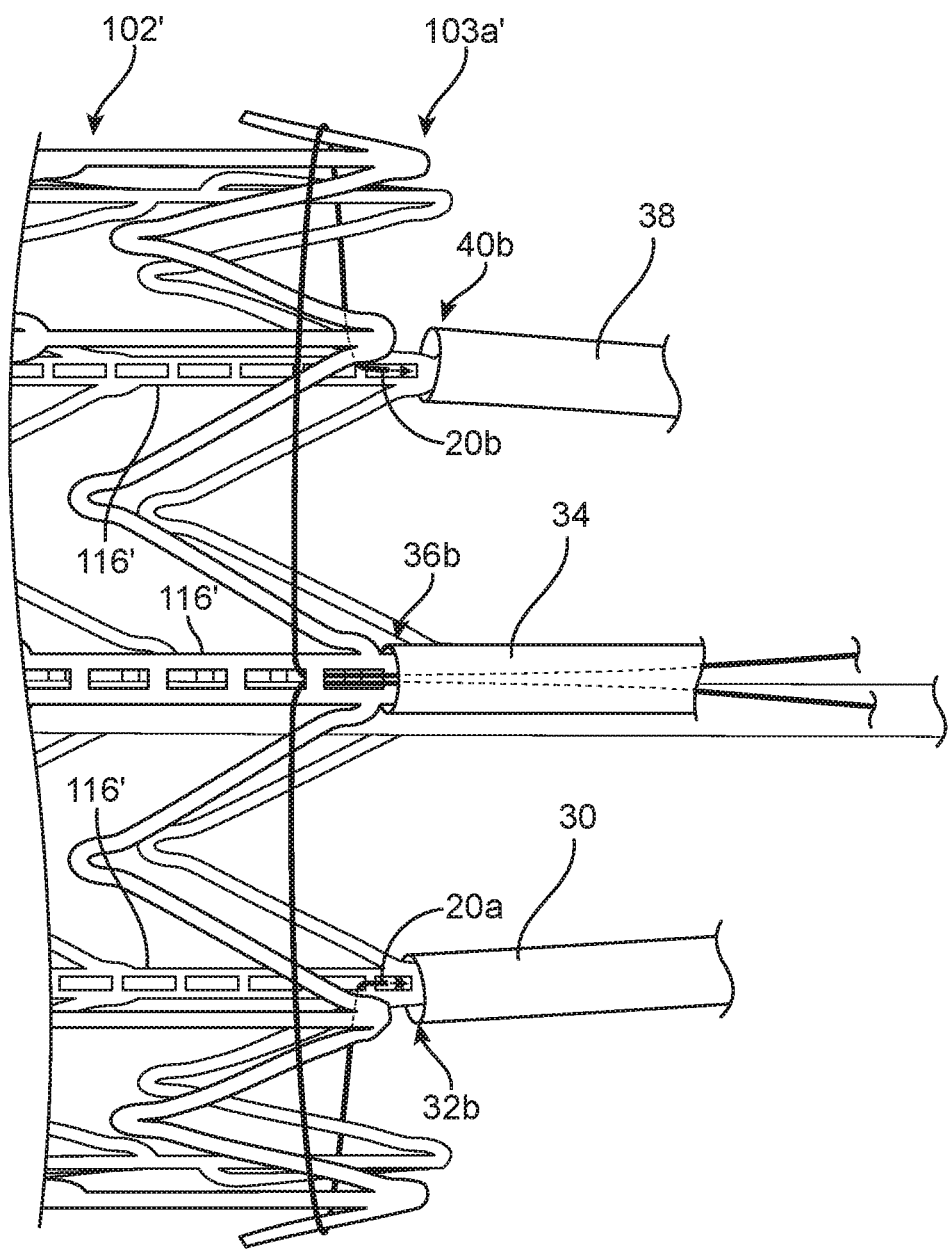
Figure 6G:
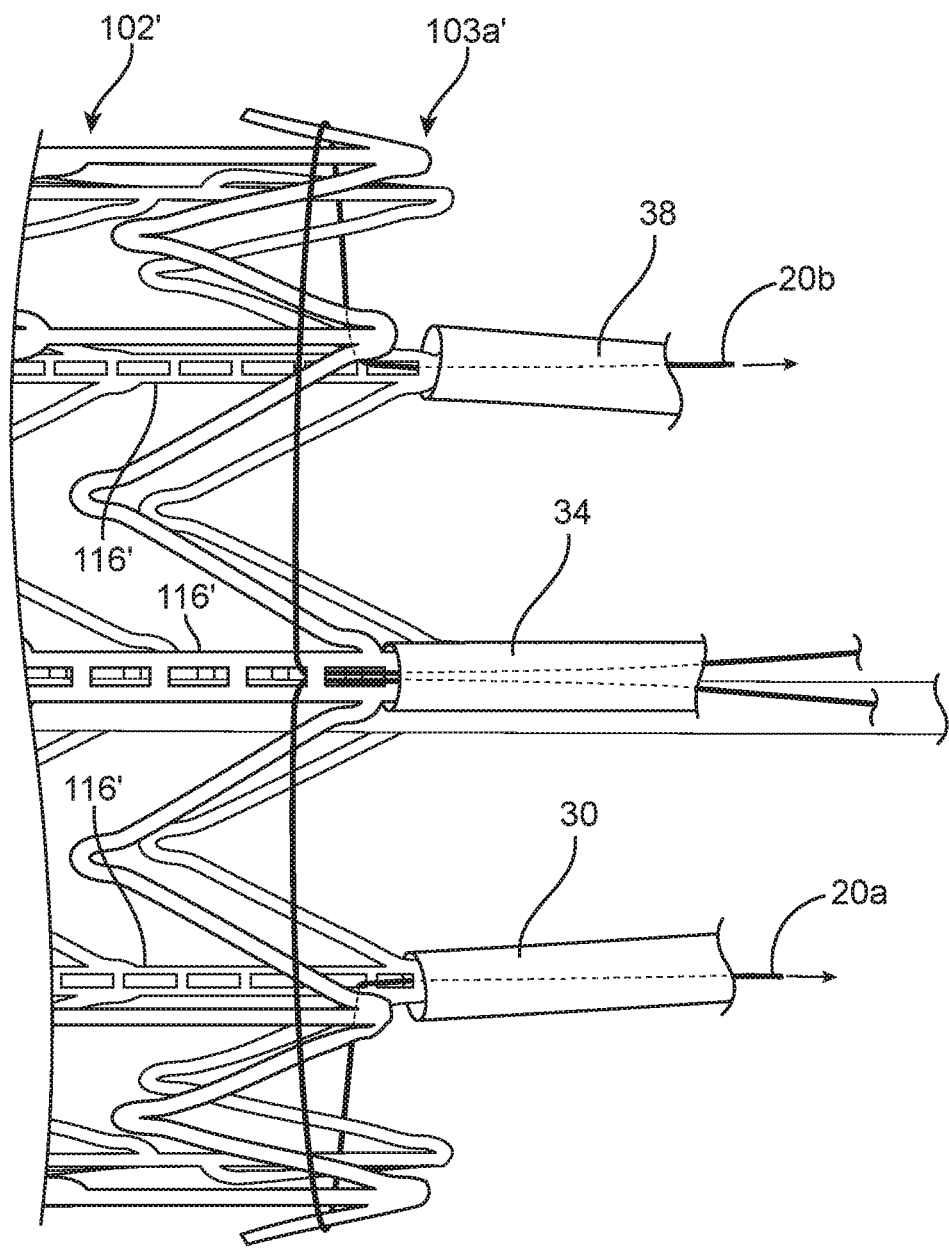
Figure 6H:
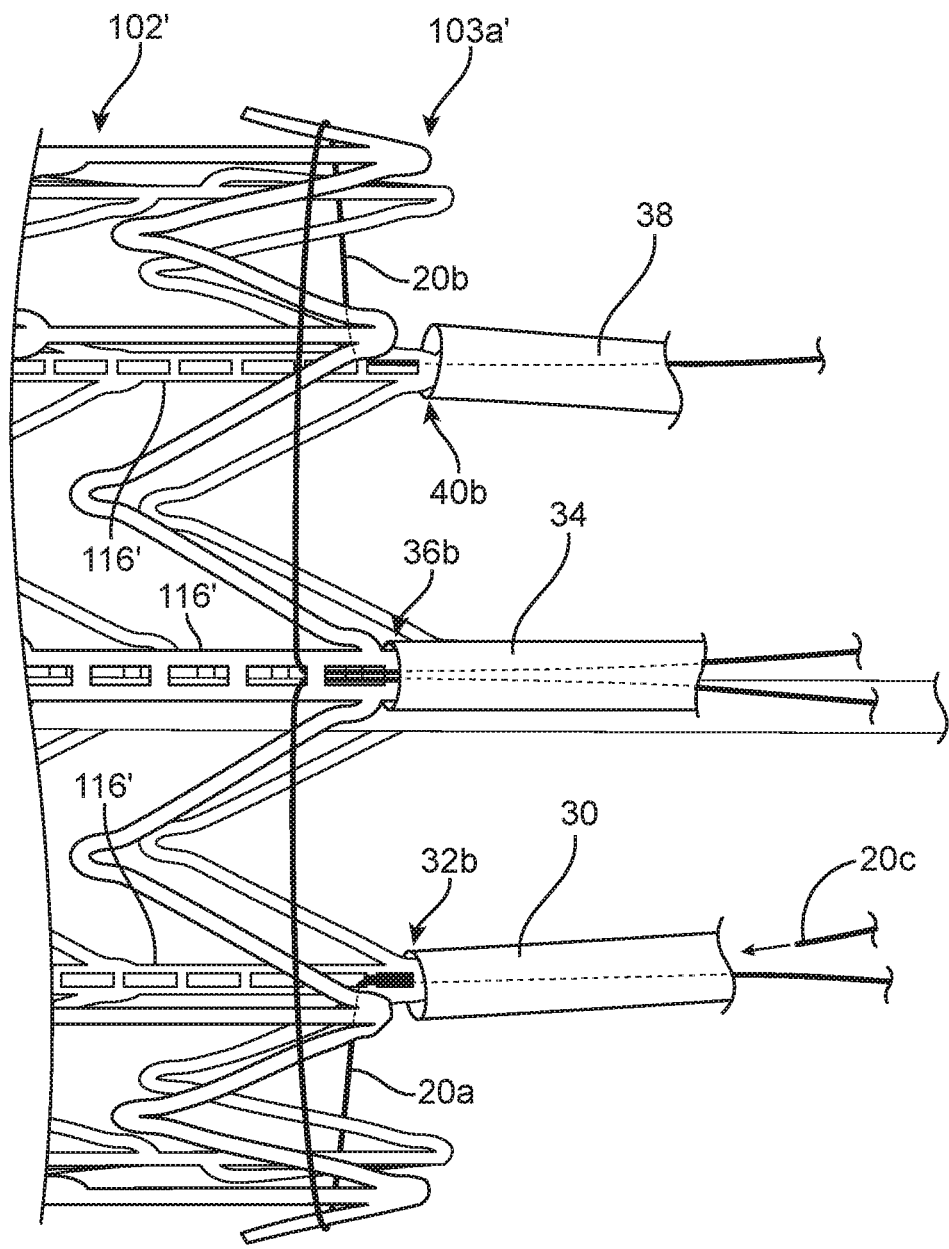
Figure 6I:
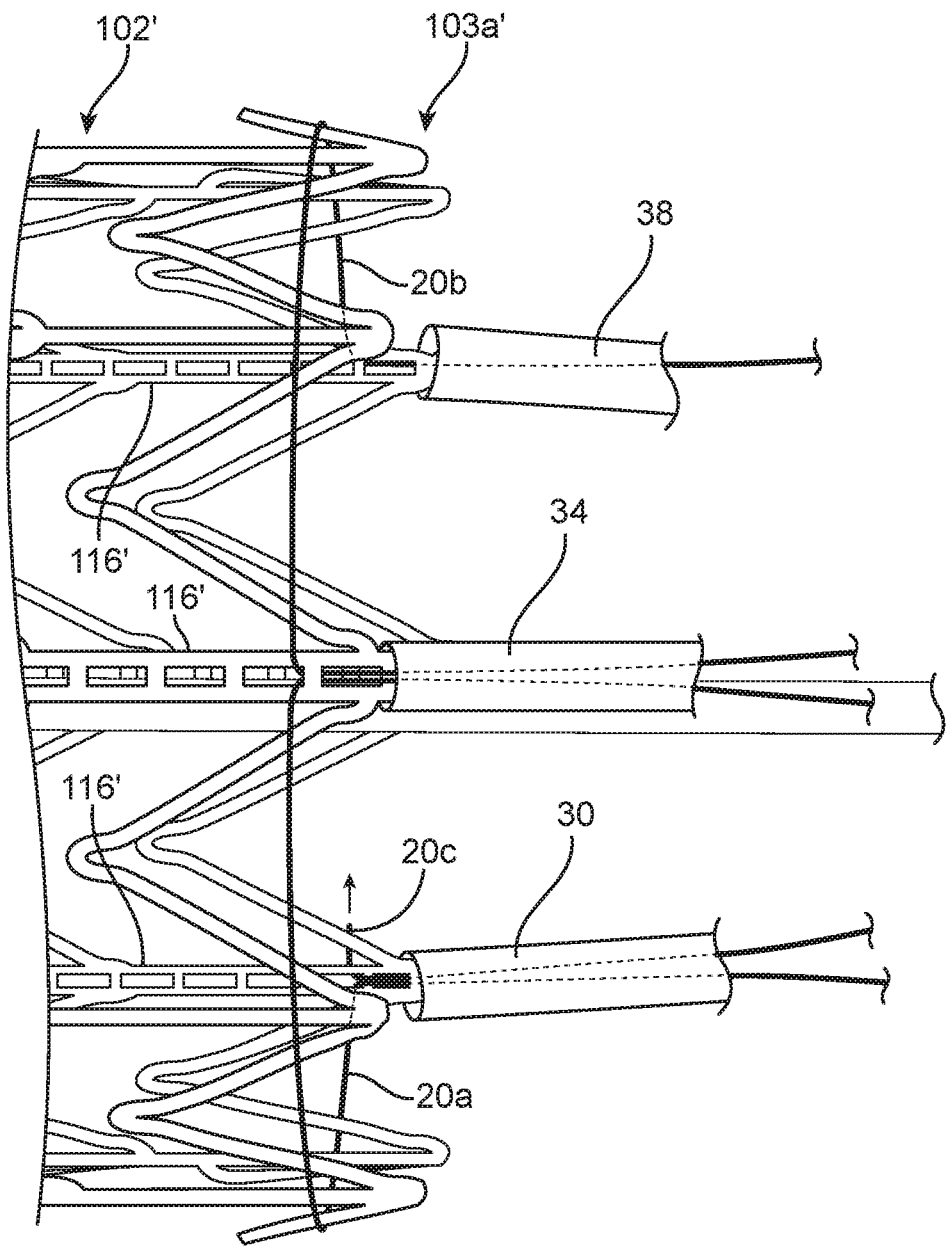
Figure 6J:
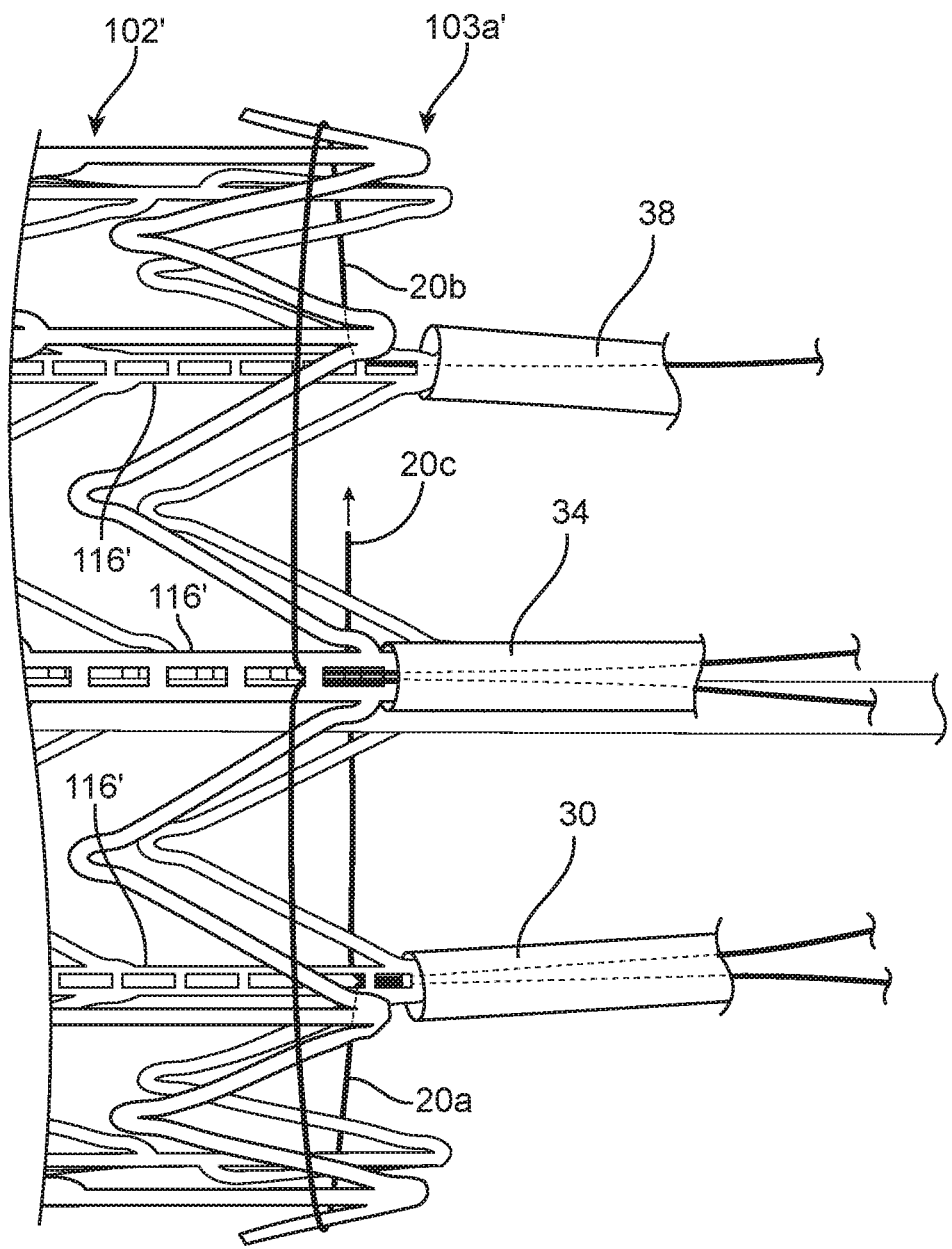
Figure 6K:
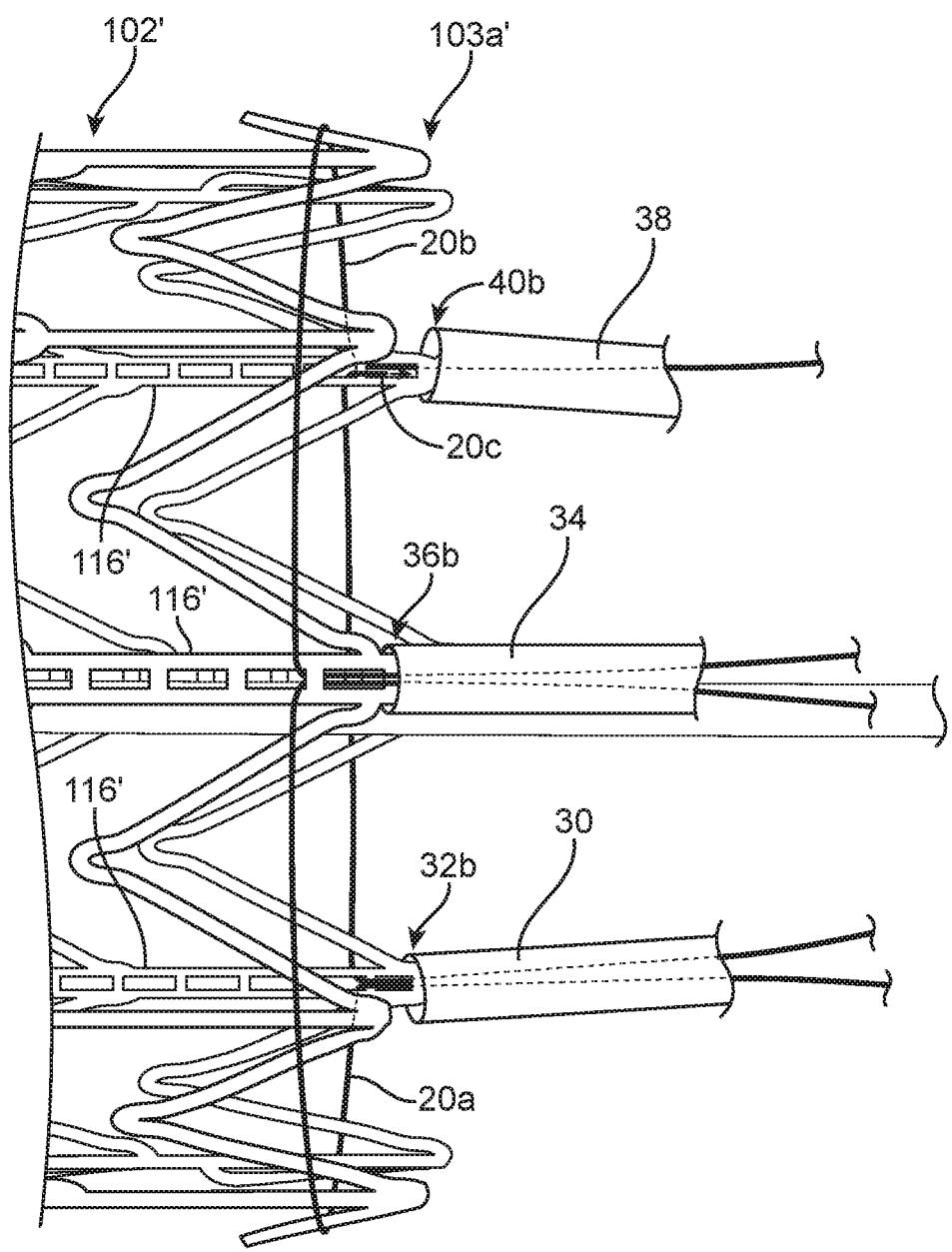
Figure 6L:
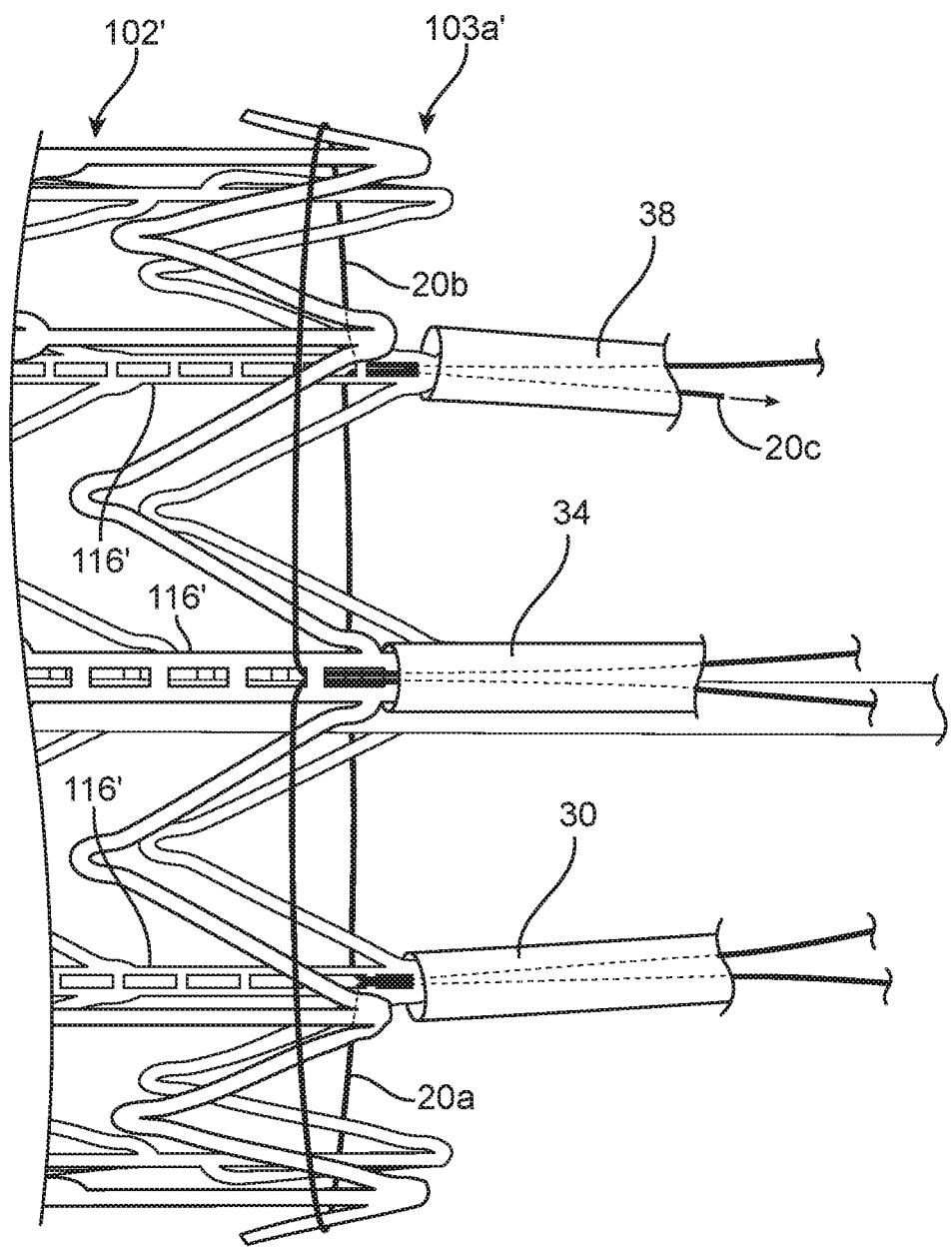

Portions of an alternate delivery device 10' and suture routing method are schematically depicted in FIG. 6A. As indicated with reference numerals, the delivery device 10' of FIG. 6A is largely similar to that of FIGS. 5A-5I with the exception of the method of routing sutures. In this embodiment, two sets of three sutures 20a-c, 24a-c are provided at the proximal end 103a' and the distal end 103b', respectively, of the stent frame 102' (i.e. three proximal sutures 20a-c and three distal sutures 24a-c). Each respective suture 20a-c, 24a-c spans approximately one third of the circumference of the stent frame 102'. Although six sutures are illustrated in this embodiment, there may be fewer or more sutures and the position of said sutures can also be varied, as desired.

One possible method of suture routing is summarized as follows. As generally illustrated in FIGS. 6B-6L, first proximal suture 20a is threaded from the proximal end 36a of the second tube 34 to the stent frame 102' and then the first proximal suture 20a is woven into adjacent post 116'. Then, the first proximal suture 20a is threaded around approximately one third of the circumference of the stent frame 102' at the proximal end 103a' until the first proximal suture 20a reaches adjacent first tube 30. The first proximal suture 20a is then threaded from the distal end 32b to the proximal end 32a of first tube 30 and finally connected to a release mechanism (not shown), such as the release mechanism 70 of FIGS. 7B-7C. The second proximal suture 20b can be threaded from the proximal end 36a to the distal end 36b of the second tube 34 and then around approximately one third of the circumference of the stent frame 102' in the direction opposite of the first proximal suture 20a. The second proximal suture 20b is then routed from the distal end 40b of the third tube 38 to the proximal end 40a for connection to a release mechanism (not shown), such as the release mechanism 70 of FIGS. 7B-7C. The third proximal suture 20c can be routed, for example, by threading the third proximal suture 20c from the proximal end 32a to the distal end 32b of the first tube 30, around or through adjacent post 116' and then around the remaining one third circumference of the stent frame 102' to the distal end 40b of the third tube 38. The third proximal suture 20c can then be routed down through the third tube 38 to the proximal end 40a of the third tube 38 and finally connected to a release mechanism (not shown), such as the release mechanism 70 of FIGS. 7B-7C. The release mechanism 70, as is further discussed below, is arranged and configured to provide tensioning and release action of the sutures 20a-c to correspondingly accommodate delivery of the prosthetic valve in a compressed state and transition of the prosthetic valve to an expanded state for implantation. There are many ways in which threading of the proximal sutures 20a-c can be accomplished such that each suture 20a-c respectively traverses approximately one third of the proximal end 103a' of the stent frame 102' and tracks through two adjacent tubes 30, 34, 38.

The first, second and third distal sutures 24a-c can be routed similar to the proximal sutures 20a-c but the distal sutures 24a-c extend from respective tubes 30, 34, 38, along the respective posts 116', to the distal end 103b' of the stent frame 102'. It is envisioned that fewer or more sutures can be utilized. The delivery device 10' can be used with or without a capsule (not shown), such as capsule 8 of FIG. 1.

The delivery devices 10, 10' described above with respect to FIGS. 5A-6L are adjustable as long as the sutures 20, 22, 24, 20a-c are attached (i.e. have not been released by the respective release mechanism 70 to deploy the prosthetic valve). To adjust the expansion and contraction of the prosthetic valve, the tension in the sutures 20, 22, 24, 20a-c is varied. In various embodiments, the tension is varied with the release mechanism 70, as discussed in detail below.

As indicated above, the delivery devices disclosed herein can include one or more release mechanisms 70 such as that disclosed in FIGS. 7A-7C. As a point of reference, FIGS. 7A-7C illustrate the release mechanism 70 aligned with the first tube 30 and interfacing with the suture 22 routed through the first tube 30. It will be understood that multiple sutures can be threaded through the first tube 30 and that the release mechanism 70 can control each of the sutures within the respective tube. Further, though not shown in FIGS. 7B-7C, additional identically configured release mechanisms can be provided within the second and third tubes 32, 34, respectively. The release mechanism 70 includes a release pin 72 within an actuation tube 74. The release pin 72 and the actuation tube 74 extend to a handle assembly (not shown), such as handle assembly 5 of FIG. 1, wherein the handle assembly actuates movement of the release pin 72 and of the actuation tube 74 within shaft 42. When the actuation tube 74 is retracted proximally relative to the tube 30, the respective suture 20 is tensioned. When the actuation tube 74 is moved distally relative the tube 30, tension in the respective suture 22 is relieved. The actuation tube 74 defines first and second cutaway sections 76a, 76b. In the illustrated embodiment, the release pin 72 is secured against a stop 78 positioned proximate the first cutaway section 76a. Alternatively, the release pin 72 can extend through a hole (not shown) in the end of the stop 78 and, in some embodiments, beyond the end of the actuation tube 74. The suture 20 has two ends. One end defines a first loop 23a that is releasably secured within the first cutaway section 76a, between the stop 78 and the pin 72. The second end defines a second loop 23b that is coupled over the pin 72 and captured in the second cutaway section 76b. The release pin 72 is slidable between a first position (as shown in FIG. 7C), in which the release pin 72 is secured against the stop 78, and a second position in which the release pin 72 is retracted proximally such that the first loop 23a is freed from confinement between the stop 78 and the release pin 72. When the first loop 23a is released from the confines between the stop 78 and the release pin 72, the respective suture 22 can be disconnected from the stent frame 102'. The stop 76 can optionally include a sloped surface 80 to ease the release of the suture 22 up and over the stop 78 when the release pin 72 is proximally retracted.

FIGS. 8A-8D illustrate select portions of yet another delivery device 10". The delivery device 10" is largely similar to that of the prior embodiments and is configured and arranged for maintaining a prosthetic valve for delivery and deployment to a defective naive heart valve (only the stent frame 102' of the prosthetic valve is shown for ease of illustration). The delivery device 10" includes tubes 30', 34',

38'. The tubes 30', 34', 38' each provide a lumen 46a through which one respective suture 20, 22, 24 can be routed between respective proximal 32a', 36a', 40a' and distal ends 32b', 36b', 40b'. The tubes 30', 34', 38' can also include a passageway 46b for receiving a pull pin 48, and a blind pocket 46c for receiving a feature of the stent frame 102'. The sutures 20, 22, 24 then collectively encircle the stent frame 102' at the proximal, intermediate and distal locations such that when the sutures 20, 22, 24 are tensioned, the stent frame 102' collapses for delivery.

One method for routing of the proximal suture 20 is summarized as follows. The first proximal suture 20 is routed through the lumen 46a from the proximal end 32a' to the distal end 32b' of the first tube 30'. Upon exit from the distal end 32b' the proximal suture 20 is threaded through one respective loop 21 proximate the adjacent post 116' that maintains the position of the proximal suture 20 prior to release. The proximal suture 20 is then wrapped around about one-third of the stent frame 102' and then around the pull pin 48 proximate the second tube 34'. The proximal suture 20 the wraps back around the entire circumference (i.e. 360 degrees) of the stent frame 102' back to the second tube 34' and then loops again around the pull pin 48. Then, the proximal suture 20 wraps back around two-thirds of the stent frame 102' to the first tube 30'. The proximal suture 20 is then routed back down the lumen 46a of the first tube 30' to a handle assembly, such as the handle assembly 5 of FIG. 1, which is arranged and configured to adjust tension in the suture 20 as well as remove the suture 20 for detaching from the stent frame 102'. The sutures 20, 22, 24 and the release pins 48 can be attached to separate or joint actuation mechanisms in the handle assembly. In alternate embodiments, the sutures 20, 22, 24 and release pins 48 may connect at a hub (not shown) positioned distal to the handle assembly. When the sutures 20, 22, 24 are routed in this way, the proximal suture 20 provides for a double wrap or thickness of suture extending around the proximal end 103a' of the stent frame 102', which provides for greater leverage when compressing the stent frame 102' as compared to a configuration having a single wrap or thickness of each suture 20. Additionally, it is believed that the retraction of the release pin and subsequent removal of the proximal suture 20 via the handle assembly is more stable due to the more even distribution of forces around the stent fame 102' during suture 20 retraction.

It will be understood that the intermediate and distal sutures 22, 24 can be routed in a similar manner. The intermediate suture 22 originating from the second tube 34' and the distal suture 24 originating from the third tube 38'. The proximal, intermediate and distal sutures 20, 22, 24 wrap around the stent frame 102' to circumscribe the stent frame 102' so that tensioning of the sutures 20, 22, 24 compress the respective portion of the stent frame 102' and a loosening of that tension allows the stent frame 102' to correspondingly expand. It will further be understood that variations in the order in which the sutures 20, 22, 24 can be routed are possible while still achieving a substantially similar result (wrapping the circumference of a stent frame with at least one a double layer of a single suture that originates from a single tube and switchbacks at a release pin).

Once the prosthetic valve is expanded and ready for deployment, the sutures 20, 22, 24 can be released from the stent frame 102' by proximally retracting the release pins 48 to disengage the release pin 48 from the respective loops 21 and sutures 20, 22, 24. The handle assembly is also actuated so that the sutures 20, 22, 24, as they actuate proximally, will unwrap from the stent frame 102' and can be withdrawn upon retraction of the delivery device 10''', leaving the deployed prosthetic valve at the defective native heart valve.

Figure 9A:
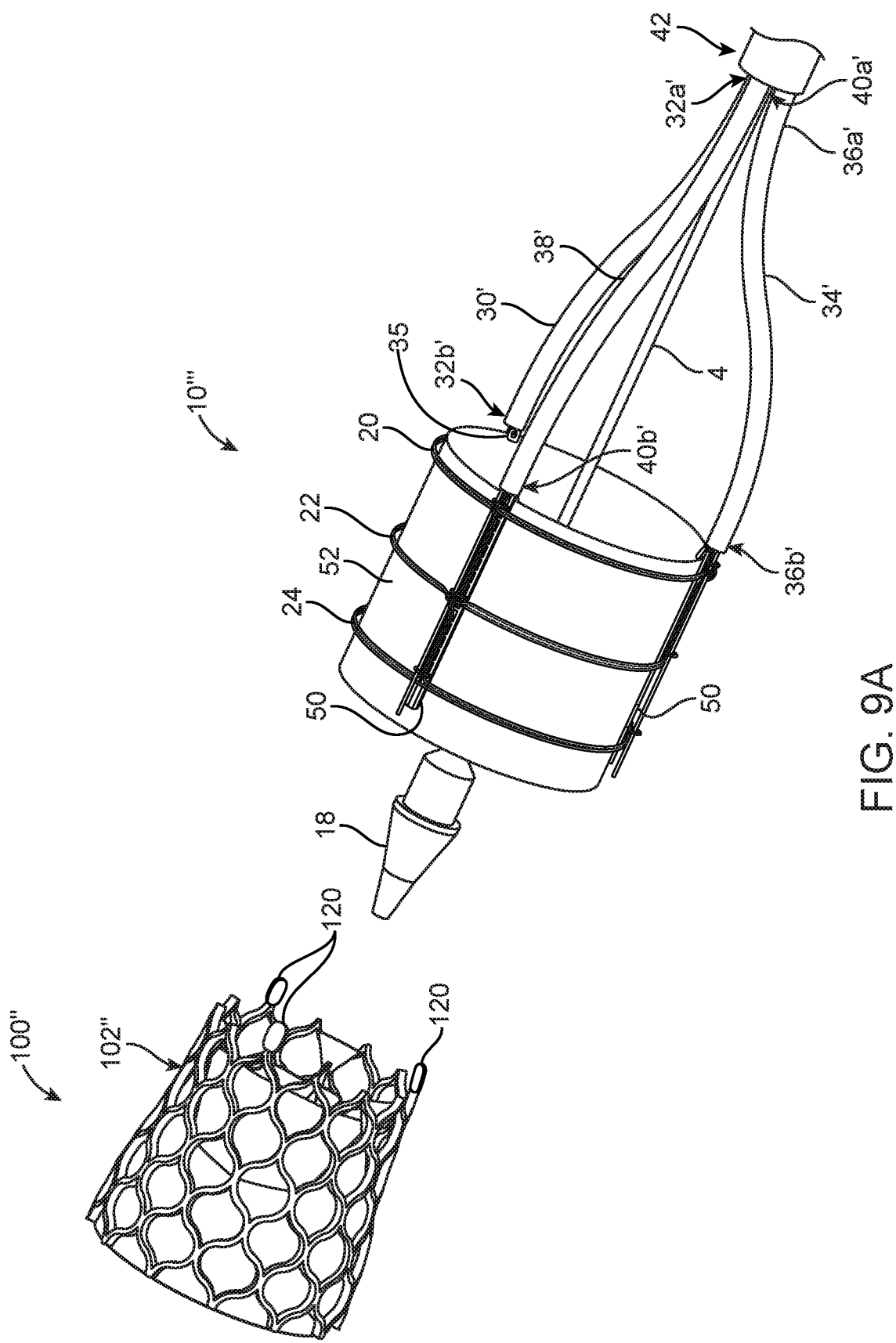
FIG. 9A is a partially exploded, perspective view of select components of an alternate delivery device.

Select components of yet another delivery device are illustrated in FIGS. 9A-9B. This delivery device 10''' is substantially similar to that of FIGS. 8A-8D but is modified for delivering and deploying a prosthetic valve 100'' that does not include rigid structures positioned along the length of its stent frame 102'' (e.g., posts 116'). In this embodiment, a rigid post 50 is fixed to the distal end 32b', 36b', 40b' of each of the tubes 30', 34', 38' or, alternatively, one rigid post 50 could be slidably positioned within each respective tube 30', 34', 38' alongside features of the stent frame 102'' (e.g., paddles 120). In this way, the rigid posts 50 are provided as part of the delivery device 10''' and not as part of the prosthetic valve 100''. Additionally, one stay suture 21 is provided at each suture 20, 22, 24 loop level (i.e. proximal, intermediate, distal) on every post 50 to maintain the position of the respective suture 20, 22, 24. The number of posts 50 provided can vary as to balance suture management and control with an increase in profile of the delivery device 10'''. The delivery device 10''' further employs a loading cylinder 52 secured to the posts 50 by sutures 35 to help manage the sutures 20, 22, 24 so that the prosthetic valve 100'' can easily be inserted into the cinching mechanism, which formed at least in part by the posts 50 and sutures 20, 22, 24. The loading cylinder 52 can be made of a thin-walled rigid or semi-rigid material. Once the prosthetic valve 100'' is in loading position, sutures 35 can be transferred to the paddles 120 to help anchor the prosthetic valve 100'' to the delivery device 10'''. The paddles 120 are shown in FIG. 9B rotated slightly for clarity; ideally, each paddle would be located near a tube 30', 34', 38' during loading. The sutures 35 would then be removed as the last step of deployment. Sutures and paddles are described here as the anchoring method; however, there are other methods that could be employed, examples include: snaps, barbs, magnets, hooks or other common fastening methods. The delivery device 10''' is otherwise configured and operates as discussed above with respect to the embodiment of FIGS. 8A-8D.

Although the present disclosure has been described with reference to preferred embodiments, workers skilled in the art will recognize that changes can be made in form and detail without departing from the spirit and scope of the present disclosure. The present disclosure is not intended to be limited to the exact configuration and order shown and described herein.

What is claimed is:

1. A combination prosthetic heart valve and delivery device for delivering the prosthetic heart valve, the combination comprising:
   a prosthetic heart valve having a frame and three posts;
   a delivery device having a guide shaft and first, second and third tubes extending therefrom; each tube having a proximal end and a distal end; wherein the distal end of each tube can receive one of the posts of the prosthetic heart valve; and
   a first length of suture extending through the first tube; wherein the first length of suture is threaded from the proximal end of the first tube to the prosthetic heart valve and around approximately one third of the circumference of the frame and then threaded through the second tube;
   a second length of suture extending from the proximal end of the second tube to the prosthetic heart valve and around approximately one third of the circumference of the frame and then extending through the third tube; and a third length of suture extending from the proximal end of the third tube to the prosthetic heart valve and around approximately one third of the circumference of the frame and then extending through the first tube.

2. The combination of claim 1, further comprising a release mechanism releasably connected to the first length of suture.

3. The combination of claim 2, wherein the second length of suture and the third length of suture are releasably connected to the release mechanism.

4. The combination of claim 2, wherein the release mechanism includes an actuation tube having first and second cutaway sections, the first length of suture positioned within at least one of the cutaway sections, the release mechanism further including a release pin slidably positioned within the actuation tube and the cutaway sections.

5. The combination of claim 4, wherein the first length of suture includes first and second closed loops, wherein the release pin is threaded through the first and second closed loops.

6. A combination prosthetic heart valve and delivery device for delivering the prosthetic heart valve, the combination comprising:

a prosthetic heart valve having a frame and three posts;

a delivery device having a guide shaft and first, second and third tubes extending therefrom; each tube having a proximal end and a distal end; wherein the distal end of each tube can receive one of the posts of the prosthetic heart valve;

a first length of suture extending through the first tube; wherein the first length of suture is threaded from the proximal end of the first tube to the prosthetic heart valve and around approximately one third of the circumference of the frame and then threaded through the second tube;

a second length of suture extending from the proximal end of the second tube to the prosthetic heart valve and around approximately one third of the circumference of the frame and then extending through the third tube;

a third length of suture extending from the proximal end of the third tube to the prosthetic heart valve and around approximately one third of the circumference of the frame and then extending through the first tube; and a release mechanism, the release mechanism including an actuation tube having a first cutaway section, the first length of suture positioned within the first cutaway section, the release mechanism further in including a pin slidably positioned within the actuation tube and the first cutaway section.

7. The combination of claim 6, wherein the release mechanism includes a second cutaway section, the first length of suture positioned within the second cutaway section, the pin slidably positioned within the second cutaway section.

8. The combination of claim 6, wherein the first length of suture includes first and second closed loops, wherein the pin is threaded through the first and second closed loops.

9. The combination of claim 6, wherein the second length of suture and the third length of suture are releasably connected to the release mechanism.

* * * * *